US011454485B2

(12) United States Patent
Pfefferkorn et al.

(10) Patent No.: US 11,454,485 B2
(45) Date of Patent: Sep. 27, 2022

(54) SYSTEMS, DEVICES AND METHODS FOR CONSISTENTLY AND UNIFORMLY MEASURING THE DIAMETERS OF SUTURES

(71) Applicant: Ethicon, Inc., Somerville, NJ (US)

(72) Inventors: Matthew Pfefferkorn, Bridgewater, NJ (US); Elizabeth Vailhe, Hillsborough, NJ (US); Kevin Hengst, Phillipsburg, NJ (US); Michael Logue, New Hope, PA (US)

(73) Assignee: Ethicon, Inc., Raritan, NJ (US)

( * ) Notice: Subject to any disclaimer, the term of this patent is extended or adjusted under 35 U.S.C. 154(b) by 744 days.

(21) Appl. No.: 16/445,311

(22) Filed: Jun. 19, 2019

(65) Prior Publication Data

US 2020/0400418 A1 Dec. 24, 2020

(51) Int. Cl.
*G01B 5/08* (2006.01)
*A61B 17/06* (2006.01)
*A61B 17/00* (2006.01)

(52) U.S. Cl.
CPC .......... *G01B 5/08* (2013.01); *A61B 17/06166* (2013.01); *A61B 2017/00725* (2013.01)

(58) Field of Classification Search
CPC .... G01B 5/08; G01B 21/10; A61B 17/06166; A61B 2017/00725
See application file for complete search history.

(56) References Cited

U.S. PATENT DOCUMENTS

| 10,251,641 | B2 | 4/2019 | Lenihan et al. | |
| 10,271,964 | B1* | 4/2019 | Samaniego | G01L 1/04 |
| 11,054,343 | B2* | 7/2021 | Kumar | G09B 23/32 |
| 2020/0072708 | A1* | 3/2020 | Kumar | G01M 99/007 |

(Continued)

FOREIGN PATENT DOCUMENTS

| CN | 201637398 | 11/2010 |
| CN | 201974136 | 9/2011 |
| CN | 205482817 | 8/2016 |

(Continued)

OTHER PUBLICATIONS

United States Pharmacopeia—861—Sutures—Diameter, https://www.uspnf.com, 2 pages.

(Continued)

*Primary Examiner* — Yaritza Guadalupe-McCall

(57) ABSTRACT

A system for measuring the diameter of a suture includes a test bench, a first suture clamping assembly slidably mounted to the test bench, and a second suture clamping assembly fixed to the test bench. The system includes a suture diameter gauge slidably mounted to the test bench and located between the first and second suture clamping assemblies for obtaining suture diameter measurements for a suture secured to the clamping assemblies. The system has a rotation assembly coupled with the first and second suture clamping assemblies for simultaneously rotating the first and second suture clamping assemblies on an axis between a first position and a second position that defines a right angle with the first position. The system includes a suture tensioning assembly for applying tension to a suture secured to the first and second suture clamping assemblies as the suture is rotated on its axis.

21 Claims, 32 Drawing Sheets

(56) References Cited

U.S. PATENT DOCUMENTS

2020/0400418 A1* 12/2020 Pfefferkorn .............. G01B 5/08

FOREIGN PATENT DOCUMENTS

| | | | | |
|---|---|---|---|---|
| CN | 106289142 | | 1/2017 | |
| CN | 206281449 | | 6/2017 | |
| CN | 206724929 | | 12/2017 | |
| JP | 2002192231 | | 7/2002 | |
| WO | WO-2020254908 A1 * | 12/2020 | ....... A61B 17/06166 |

OTHER PUBLICATIONS

United States Pharmacopeia—871—Sutures—Needle Attachment, https://www.uspnf.com, 2 pages.
United States Pharmacopeia—881—Tensile Strength, https://www.uspnf.com, 3 pages.
International Search Report issued in corresponding International Application No. PCT/IB2020/055333, dated Sep. 8, 2020, 5 pages.

* cited by examiner

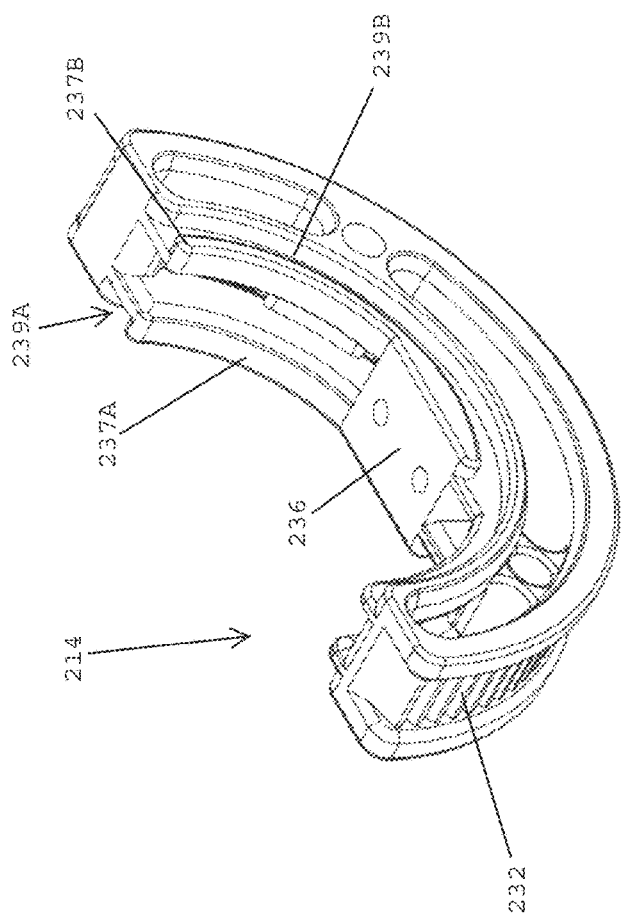
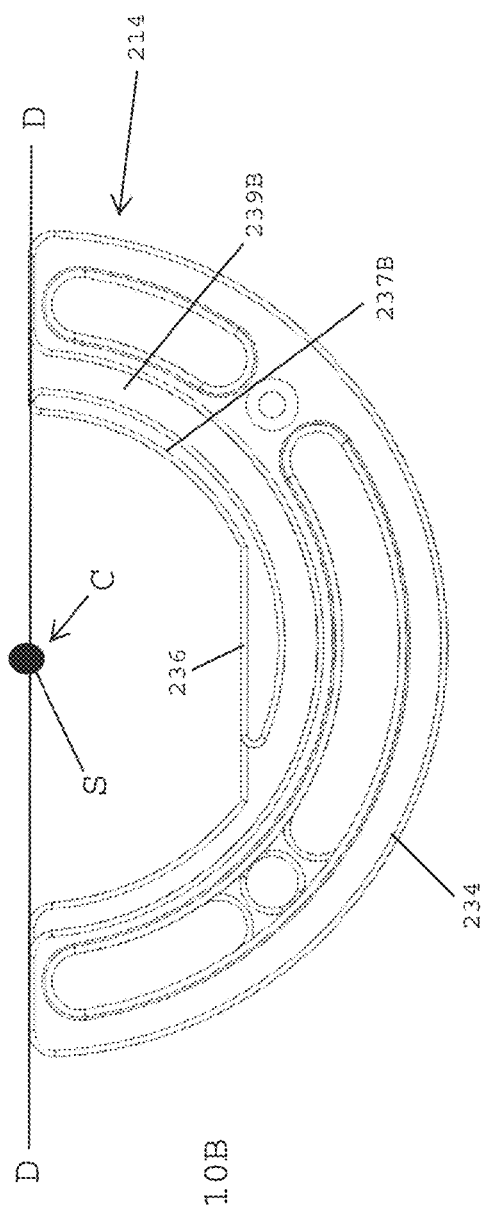
FIG. 10A
FIG. 10B

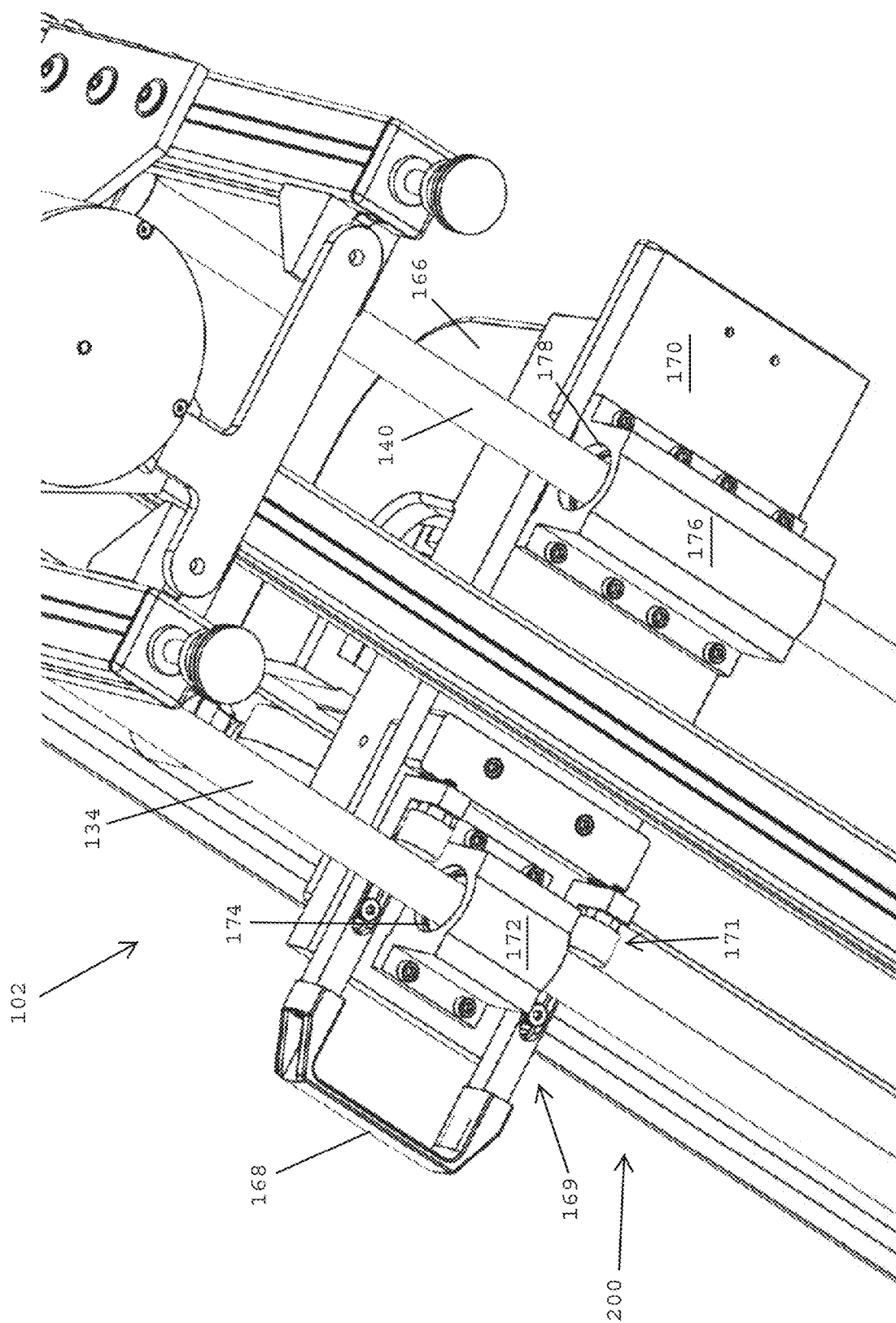

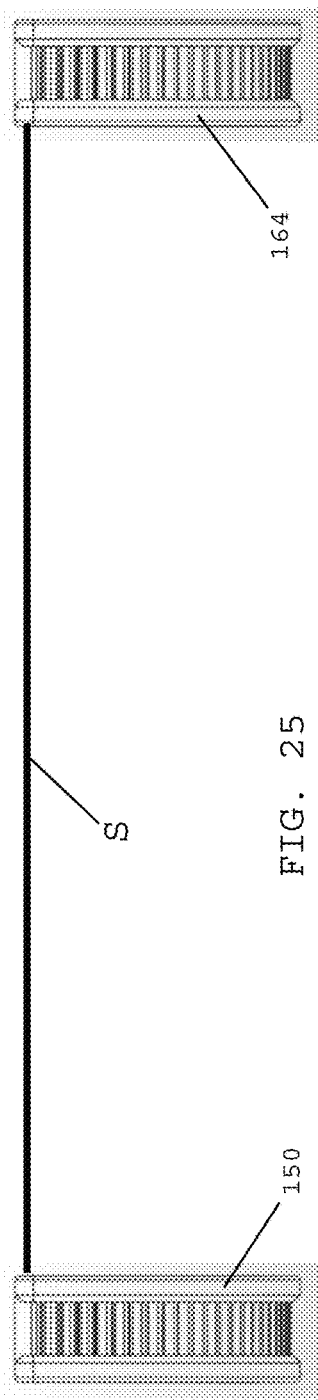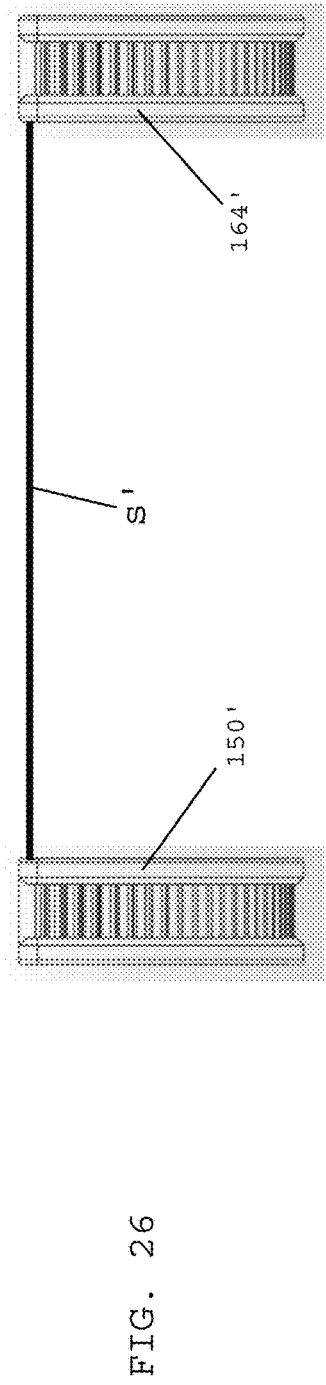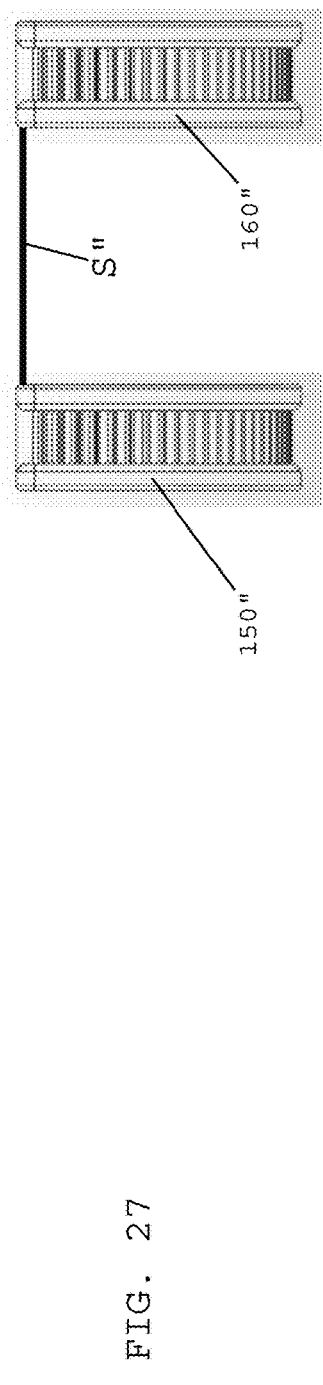

SYSTEMS, DEVICES AND METHODS FOR CONSISTENTLY AND UNIFORMLY MEASURING THE DIAMETERS OF SUTURES

BACKGROUND OF THE INVENTION

Field of the Invention

The present patent application is generally related to surgical sutures, and is more specifically related to systems, devices and methods for measuring the diameters of sutures such as braided or multifilament sutures.

Description of the Related Art

Surgical sutures are used to close wounds and surgical incisions, and to repair damaged or severed muscles, vessels, and tissue. Typically, the suture is attached at one end to a needle, and the needle is drawn through tissue to form one or more loops holding the tissue together. The suture is subsequently tied off using one or more knots so that the tissue will remain drawn together.

Although conventional sutures have proven to be very effective and reliable for closing wounds, additional types sutures have been developed for use during certain kinds of medical procedures. One such suture, known as a barbed suture, has barbs that project outwardly from a filament, which allows the suture to be used to close wounds, approximate tissue, tighten tissue, and attach prosthetic devices—all without using knots.

Sutures should be flexible, strong, non-breakable, non-toxic, and non-hypoallergenic. In addition, sutures should not promote wicking, which means that sutures must not allow fluids to penetrate the body or organ from the outside.

Sutures may be made of bioabsorbable materials, which are absorbed by the body over time, and non-bioabsorbable materials, which are either left indefinitely in the body or are removed manually by medical personnel. The exact type of surgical suture that should be used (i.e., bioabsorbable or non-bioabsorbable) depends upon the operation, with a major criterion being the location of the incision.

The United States Pharmacopeia (USP). The USP is a compendium of information for the United States, which is published annually by the United States Pharmacopeial Convention. The USP is the official standards-setting authority for pharmaceutical products and medical devices including establishing standards for surgical sutures.

Sutures are required to meet predetermined performance standards, which are set forth in USP. For example, the USP establishes the different sizes for sutures. According to the USP, sutures can be manufactured is various sizes ranging from #10 to #12-0, where #5 corresponds with a heavy braided suture used for orthopedics, while #10/0 is a fine monofilament suture used for ophthalmic applications. The actual diameter of a thread for a given USP suture size differs depending upon the class of the suture material.

The USP also defines the mechanical suture testing standards that are required for testing, evaluating, and measuring surgical sutures. The USP mechanical suture testing standards include USP 861—Suture Diameter, USP 871—Needle Attachment, and USP 881—Tensile Strength.

USP 861 establishes the type of gauge that must be used when measuring the diameter of a suture. For collagen sutures, USP 861 directs that the gauge for determining the diameter of a suture be of a dead-weight type. For all suture types, USP 861 directs: 1) that the presser foot and moving parts connected with the gauge be weighted so as to apply a total load of 210±3 g to the suture specimen; and 2) that when measuring the diameter of a suture of metric size 0.4 and smaller, that additional weight should be removed from the presser foot so that the total load applied to the suture does not exceed 60 g.

USP 861 also directs using the following guidelines for measuring the diameter of a suture specimen: 1) determining the diameter immediately after removing the suture from its container and without stretching the suture; 2) laying the suture strand across the center of an anvil and presser foot, and gently lowering the presser foot until its entire weight rests upon the suture; and 3) measuring the diameter of each suture specimen at three points that correspond roughly to one-fourth, one-half, and three-fourths of the length of the suture specimen.

For multifilament sutures larger than 3-0, USP 861 also requires two diameter measurements at each point along the length of the suture specimen, with the diameter measurements being at right angles to one another, and using the average of the two measurements as the observed diameter at that point.

There are a number of deficiencies that arise when using USP 861 for measuring the diameters of sutures. In particular, using a dead-weight gauge to drop a weight directly onto a suture strand may permanently compress and/or damage the suture strand, which could result in obtaining inaccurate diameter measurements for sutures. In addition, USP 861 provides no consistent and repeatable standard for controlling the rate of descent of the dead-weight when lowering the dead-weight onto the suture strand. Moreover, there are no consistent standards for pre-tensioning suture specimens, for securing the ends of the suture specimens, or for controlling how the suture specimens are rotated for obtaining diameter measurements on two different sides of a suture that are at a right angle relative to one another.

In addition, multifilament sutures are required to be tensioned prior to measuring suture diameter per the USP monographs. The monographs are somewhat broad and/or vague and do not explain the exact method on how to apply tension to the suture and/or how to rotate the suture for obtaining two diameter measurements. Various diameter testing methods and machines are well known in the art, however, these known methods and machines require manual adjustments to be made by an operator and are thus not very repeatable. For example, some conventional machines require an operator to physically grasp the suture between two fingers and twist the suture by hand for rotating the suture to obtain the two diameter measurements.

Thus, in spite of the above-noted USP standards and the existing, prior art suture diameter measuring protocols, there remains a continuing need for improved systems, devices, and methods for more accurately, consistently, and repeatedly measuring the diameters of suture specimens. There also remains a need for systems, devices and methods for measuring the diameters of sutures having different lengths, and for rotating sutures for measuring the diameter of a suture on two different sides of the suture in a consistent manner.

SUMMARY OF THE INVENTION

In one embodiment, a system is designed to comply with the USP's standard compendial monographs for sutures (e.g., multifilament sutures, monofilament sutures), and provides a methodology to test suture diameter in a consistent, repeatable, and reproducible manner, thereby minimizing the impact of a human operator and/or human.

In one embodiment, a system preferably enables suture diameter measurements to be performed on suture strands having various lengths. Sutures strands having any length may be accommodated. In one embodiment, the system may accommodate suture strands having lengths of approximately six (6) to 48 inches. In one embodiment, a system for obtaining suture diameter measurements may accommodate suture strands having lengths of approximately 10 feet or greater. In one embodiment, a system for obtaining suture diameter measurements may accommodate suture strands having lengths of less than six inches (e.g., a suture having a length of one to six inches). In one embodiment, the first and second diameter readings are obtained at right angles to each other at the same point along the length of a suture strand. In one embodiment, the suture strand is preferably maintained under tension (e.g., a constant level of tension) as it is rotated for obtaining the first and second diameter readings. In one embodiment, the system desirably couples moveable clamps with a rotary feature to enable diameter measurements at right angles to each other on a suture strand. The system disclosed herein provides simple, rapid, consistent and repeatable methods for rotating both ends of a suture simultaneously to provide consistent and repeatable diameter measurement results.

The testing system disclosed herein improves upon known systems by providing for better integration, suture rotation, and measuring the diameter of the suture at several points along the length of the suture.

In one embodiment, with a first end of a suture secured to a first suture clamp and a second end of the suture secured to a second suture clamp, the system preferably includes a lever that is operatively connected to the first and second suture clamps to simultaneously rotate the first and second suture clamps together between a first position (e.g., a zero degree position), and a second position (e.g., a 90 degree position).

In one embodiment, a system for measuring the diameter of a suture preferably includes a test bench, a first suture clamping assembly slidably mounted to the test bench, a second suture clamping assembly fixed to the test bench, and a suture diameter gauge slidably mounted to the test bench and being located between the first and second suture clamping assemblies. In one embodiment, the system preferably includes a rotation assembly coupled with the first and second suture clamping assemblies for simultaneously rotating the first and second suture clamping assemblies on an axis between a first position and a second position. In one embodiment, the first position may be a zero degree position and the second position may be a 90 degree position that defines a right angle with the first position. In one embodiment, the system desirably includes a suture tensioning assembly coupled with one of the first and second suture clamping assemblies for applying tension to the suture to hold the suture taut as it is measured and rotated on its axis.

In one embodiment, the first suture clamping assembly desirably includes a first suture mounting surface, and the second suture clamping assembly desirably includes a second suture mounting surface. In one embodiment, after the ends of a suture have been secured to the respective first and second suture clamping assemblies, with the suture strand extending along an axis, the first and second suture mounting surfaces may be simultaneously rotated on the axis when moving between the first position and the second position.

In one embodiment, the first and second suture mounting surfaces preferably lie in a common horizontal plane (e.g., parallel with the floor) when the first and second suture clamping assemblies are in the first position. In one embodiment, the first and second suture mounting surfaces preferably lie in a common vertical plane (e.g., perpendicular to the floor) when the first and second suture clamping assemblies are in the second position.

In one embodiment, the first suture clamping assembly may include a first suture securing lever having a first cam surface and a first suture backstop that opposes the first cam surface. In one embodiment, the first suture securing lever is moveable between an unlocked position and a locked position for pinching a first end of a suture between the first cam surface and the first suture backstop. The rotatable cam surface enables the system to be used to mount a wide variety of sutures having varying diameters and made of different materials in order to measure suture diameter.

In one embodiment, the second suture clamping assembly may include a second suture securing lever having a second cam surface and a second suture backstop that opposes the second cam surface. In one embodiment, the second suture securing lever is moveable between an unlocked position and a locked position for pinching a second end of a suture between the second cam surface and the second suture backstop. Thus, the system may be used to mount multiple sutures with varying diameters and materials in order to measure suture diameter.

In one embodiment, a first end of a suture may be secured between the first cam surface and the first suture backstop, and a second end of the suture may be secured between the second cam surface and the second suture backstop. In one embodiment, a loop may be tied at an end of a suture and the loop placed over a post or anchor for securing the end of the suture.

In one embodiment, the test bench may include a left end plate that defines a left end of the test bench, a right end plate assembly that defines a right end of the test bench, a front guide rail interconnecting the left end plate and the right end plate assembly, and a rear guide rail interconnecting the left end plate and the right end plate assembly. In one embodiment, the front and rear guide rails desirably have respective longitudinal axes that are parallel to one another.

In one embodiment, the first suture clamping assembly is slidably mounted on the front and rear guide rails for sliding between the left end plate and the right end plate assembly. The distance between the first suture clamping assembly and the second suture clamping assembly may be adjusted to accommodate sutures having different lengths. Thus, the system may be used to measure the diameters of sutures having various lengths (e.g., sutures having lengths of 6-48 inches; sutures having lengths of 1-6 inches; sutures having lengths of 4-10 feet or greater).

In one embodiment, the suture diameter gauge is slidably mounted on the front and rear guide rails for sliding between the first suture clamping assembly and the right end plate assembly. The slidable suture diameter measuring gauge may be selectively moved to measure suture diameters at different points along the length of a suture (e.g., ¼ length, ½ length, ¾ length).

In one embodiment, the rotation assembly preferably includes a rotatable bar having a longitudinal axis. In one embodiment, the rotatable bar has a first end that is rotatably secured to the left end plate, and a second end that is rotatably secured to the right end plate assembly. In one embodiment, the rotatable bar is desirably coupled with the first and second suture clamping assemblies, whereby the rotatable bar is rotatable about the longitudinal axis thereof for moving the first and second suture clamping assemblies between the first position and the second position. In one embodiment, the first suture clamping assembly is configured to slide over the rotatable bar when adjusting the distance between the first and second suture clamping assemblies.

In one embodiment, the first suture clamping assembly desirably includes a first small gear mounted on the rotatable bar and a first large gear that meshes with the first small gear. In one embodiment, the first suture mounting surface is preferably secured to the first large gear.

In one embodiment, the second suture clamping assembly preferably includes a second small gear mounted on the rotatable bar and a second large gear that meshes with the second small gear. In one embodiment, the second suture mounting surface is preferably secured to the second large gear.

In one embodiment, rotating the rotatable bar simultaneously rotates the first and second small gears, which, in turn, simultaneously rotates the respective first and second large gears, which, in turn, simultaneously rotates the respective first and second suture mounting surfaces. In one embodiment, the ends of a suture are secured over the respective first and second suture mounting surfaces so that the suture rotates simultaneously with the first and second large gears.

In one embodiment, the system preferably includes a locking handle that may be coupled with the first suture clamping assembly. In one embodiment, the locking handle preferably has an unlocked position in which the first suture clamping assembly is free to slide over both the front and rear guide rails and the rotatable bar for adjusting a distance between the first suture clamping assembly and the second suture clamping assembly, and a locked position in which the first suture clamping assembly is locked in place to the front and rear guide rails so that it may no longer slide while locked.

In one embodiment, the first suture clamping assembly preferably includes a first outer gear plate and a first inner gear plate that contain the first small gear and the first large gear. In one embodiment, a first rotatable bar opening desirably passes through the first outer gear plate and the first inner gear plate for receiving the rotatable bar.

In one embodiment, the second suture clamping assembly preferably includes a second outer gear plate and a second inner gear plate that contain the second small gear and the second large gear. In one embodiment, a second rotatable bar opening desirably passes through the second outer gear plate and the second inner gear plate for receiving the rotatable bar.

In one embodiment, the second suture clamping assembly is fixed to an upper end of the right end plate assembly of the test bench.

In one embodiment, the test bench may include a left front leg and a left rear leg located at the left side of the test bench, and a left lateral support interconnecting upper ends of the left front leg and the left rear leg.

In one embodiment, the test bench may include a right front leg and a right rear leg located at the right side of the test bench, and a right lateral support interconnecting upper ends of the right front leg and the right rear leg.

In one embodiment, the test bench may include a longitudinal support extending along a length of the test bench and interconnecting the left and right lateral supports. The longitudinal support preferably enhances the structural integrity of the test bench.

In one embodiment, a leveling foot may be mounted at a lower end of each of the legs for adjusting respective lengths of the legs and/or for leveling the test bench over a surface (e.g., a table top, a lab bench, a floor).

In one embodiment, the suture diameter gauge preferably includes a suture testing platform having a top surface adapted to seat a suture, a test probe having a lower end that is configured to be lowered toward the top surface of the suture testing platform for measuring a diameter of the suture, a visual display for showing the measured diameter of the suture, and an actuator (e.g., a foot pedal) coupled with the suture diameter gauge and/or the test probe for electronically controlling the movement of the lower end of the test probe toward the top surface of the suture testing platform. In one embodiment, when measuring a suture diameter, the test probe is not simply dropped onto the suture, but is rather lowered onto the suture in a controlled manner that avoids damaging (e.g., deforming, squashing) the suture.

In one embodiment, a system for measuring the diameter of a suture preferably includes a test bench having a left end plate and a right end plate assembly and front and rear guide rails that extend between the left end plate and the right end plate assembly, whereby the front and rear guide rails have respective longitudinal axes that are parallel to one another.

In one embodiment, the system preferably includes a first suture clamping assembly slidably mounted to the front and rear guide rails, a second suture clamping assembly fixed to an upper end of the right end plate assembly, and a suture diameter gauge slidably mounted to the front and rear guide rails.

In one embodiment, the system desirably includes a rotatable bar coupled with the first and second suture clamping assemblies for simultaneously rotating the first and second suture clamping assemblies on an axis between a first position and a second position. In one embodiment, the first and second positions are offset from one another and may define a right angle.

In one embodiment, the system preferably includes a suture tensioning assembly coupled with the second suture clamping assembly, whereby the first suture clamping assembly is configured to slide over both the front and rear guide rails and the rotatable bar for adjusting a distance between the first suture clamping assembly and the second suture clamping assembly. In one embodiment, the suture diameter gauge is configured to slide over the front and rear guide rails and between the first and second suture clamping assemblies for obtaining suture diameter measurements at different points along the length of a suture.

In one embodiment, the rotatable bar preferably has a longitudinal axis that is parallel with the longitudinal axes of the respective front and rear guide rails. In one embodiment, the test bench is preferably leveled over a floor surface so that the guide rails and the rotatable bar are parallel with the floor surface. In one embodiment, the rotatable bar desirably has a first end that is rotatably coupled with the left end plate, and a second end that is rotatably secured to the right end plate assembly, whereby the rotatable bar is rotatable about the longitudinal axis thereof for moving the first and second suture clamping assemblies between the first position and the second position, which preferably defines a right angle with the first position.

In one embodiment, the first suture clamping assembly desirably includes a first small gear mounted on the rotatable bar, a first large gear that meshes with the first small gear, and a first suture mounting surface that is secured to the first large gear.

In one embodiment, the second suture clamping assembly desirably includes a second small gear mounted on the rotatable bar, a second large gear that meshes with the second small gear, and a second suture mounting surface that is secured to the second large gear.

In one embodiment, rotating the rotatable bar (e.g., a hex bar) simultaneously rotates the first and second small gears, which, in turn, simultaneously rotates the respective first and second large gears, which, in turn, simultaneously rotates the respective first and second suture mounting surfaces, which, in turn, rotates the suture having ends secured to the respective first and second suture clamping assemblies.

In one embodiment, the first suture clamping assembly desirably includes a first outer gear plate and a first inner gear plate that contain the first small gear and the first large gear. In one embodiment, a first rotatable bar opening passes through the first outer gear plate and the first inner gear plate for receiving the rotatable bar.

In one embodiment, the second suture clamping assembly desirably includes a second outer gear plate and a second inner gear plate that contain the second small gear and the second large gear. In one embodiment, a second rotatable bar opening desirably passes through the second outer gear plate and the second inner gear plate for receiving the rotatable bar.

In one embodiment, a method of measuring the diameter of a suture preferably includes securing a first end of a suture to a first suture clamping assembly, securing a second end of the suture to a second suture clamping assembly, and applying tension to the suture through one of the first and second suture clamping assemblies, whereby the suture under tension lies in an axis that extends from the first suture clamping assembly to the second suture clamping assembly. In one embodiment, the system may include a linear slide that is coupled with one of the first and second suture clamping assemblies, which allows the suture to stretch when tension is applied. The tension applied to the suture (e.g., half the knot-pull limit) preferably holds the suture taut as it extends along the axis between the first and second suture clamping assemblies.

In one embodiment, the method preferably includes locating a suture diameter gauge at a first point along a length of the suture (e.g., ¼ of the way along the length of the suture), using the suture diameter gauge to obtain a first diameter measurement for the suture at the first point along the length of the suture, and while continuing to apply the tension to the suture, simultaneously rotating the first and second suture clamping assemblies on the axis by 90 degrees between a first position and a second position, which, in turn, rotates the suture on its axis by 90 degrees between the first and second positions. In one embodiment, the suture diameter gauge desirably includes a brake or lock for fixing the location of the suture diameter gauge along the length of a suture, such as at the first point along the length of the suture. In one embodiment, the suture diameter gauge may be locked at different positions along the length of a suture (e.g., at ¼ of the length of the suture, at ½ of the length of the suture, at ¾ of the length of the suture), whereby first and second diameter measurements may be obtained for each location. In one embodiment, the system preferably includes a first fixed stop associated with the first rotation position of the clamping assemblies and a second fixed stop associated with the second rotation position of the clamping assemblies.

In one embodiment, the method may include using the suture diameter gauge to obtain a second diameter measurement for the suture at the first point along the length of the suture, whereby the first and second diameter measurements at the first point along the length of the suture are offset from one another. In one embodiment, the first and second suture diameter measurements are at a right angle relative to one another.

In one embodiment, the method may include simultaneously rotating the first and second suture clamping assemblies back to the first position, which, in turn, rotates the suture on the axis by 90 degrees back to the first position, moving the suture diameter gauge to a second point along the length of the suture that is spaced from the first point (e.g., ½ of the way along the length of the suture), and while continuing to apply the tension to the suture, using the suture diameter gauge to obtain a first diameter measurement for the suture at the second point along the length of the suture.

In one embodiment, a method may include while continuing to apply tension to the suture, simultaneously rotating the first and second suture clamping assemblies on the axis by 90 degrees, which, in turn, rotates the suture on the axis by 90 degrees, and using the suture diameter gauge to obtain a second diameter measurement for the suture at the second point along the length of the suture, whereby the first and second diameter measurements at the second point along the length of the suture are at a right angle relative to one another.

In one embodiment, a method may include simultaneously rotating the first and second suture clamping assemblies back to the first position, moving the suture diameter gauge to a third point along the length of the suture that is spaced from the second point (e.g., ¾ of the way along the length of the suture), and while continuing to apply the tension to the suture, using the suture diameter gauge to obtain a first diameter measurement for the suture at the third point along the length of the suture.

In one embodiment, a method may include while continuing to apply the tension to the suture, simultaneously rotating the first and second suture clamping assemblies on the axis by 90 degrees, which, in turn, rotates the suture on the axis by 90 degrees, and using the suture diameter gauge to obtain a second diameter measurement for the suture at the third point along the length of the suture, whereby the first and second diameter measurements at the third point along the length of the suture are at a right angle relative to one another.

Although some of the embodiments disclosed herein teach rotating a suture by 90 degrees for obtaining two different diameter measurements, in one embodiment, the system may rotate the suture by less than 90 degrees (e.g., 60 degrees) for obtaining the first and second suture diameter measurements, or by more than 90 degrees (e.g., 100 degrees for obtaining the first and second suture diameter measurements.

These and other preferred embodiments of the present patent application will be described in more detail below.

BRIEF DESCRIPTION OF THE DRAWINGS

FIG. 10A shows a perspective view of the first large gear shown in FIG. 9, in accordance with one embodiment of the present patent application.

FIG. 10B shows a front elevation view of the first large gear shown in FIG. 9.

FIG. 22 shows an underside of a test bench and the suture diameter measurement gauge shown in FIGS. 18-21.

FIG. 25 is a schematic view of a suture having a first end secured to a first suture clamping assembly and a second end secured to a second suture clamping assembly, wherein the first and second suture clamping assemblies are spaced from one another, in accordance with one embodiment of the present patent application.

FIG. 26 is a schematic view of the first and second suture clamping assemblies of FIG. 25 after the first suture clamping assembly has been moved closer to the second suture clamping assembly.

FIG. 27 is a schematic view of the first and second suture clamping assemblies of FIG. 26 after the first suture clamping assembly has been moved closer to the second suture clamping assembly.

DETAILED DESCRIPTION OF PREFERRED EMBODIMENTS

Figure 1:
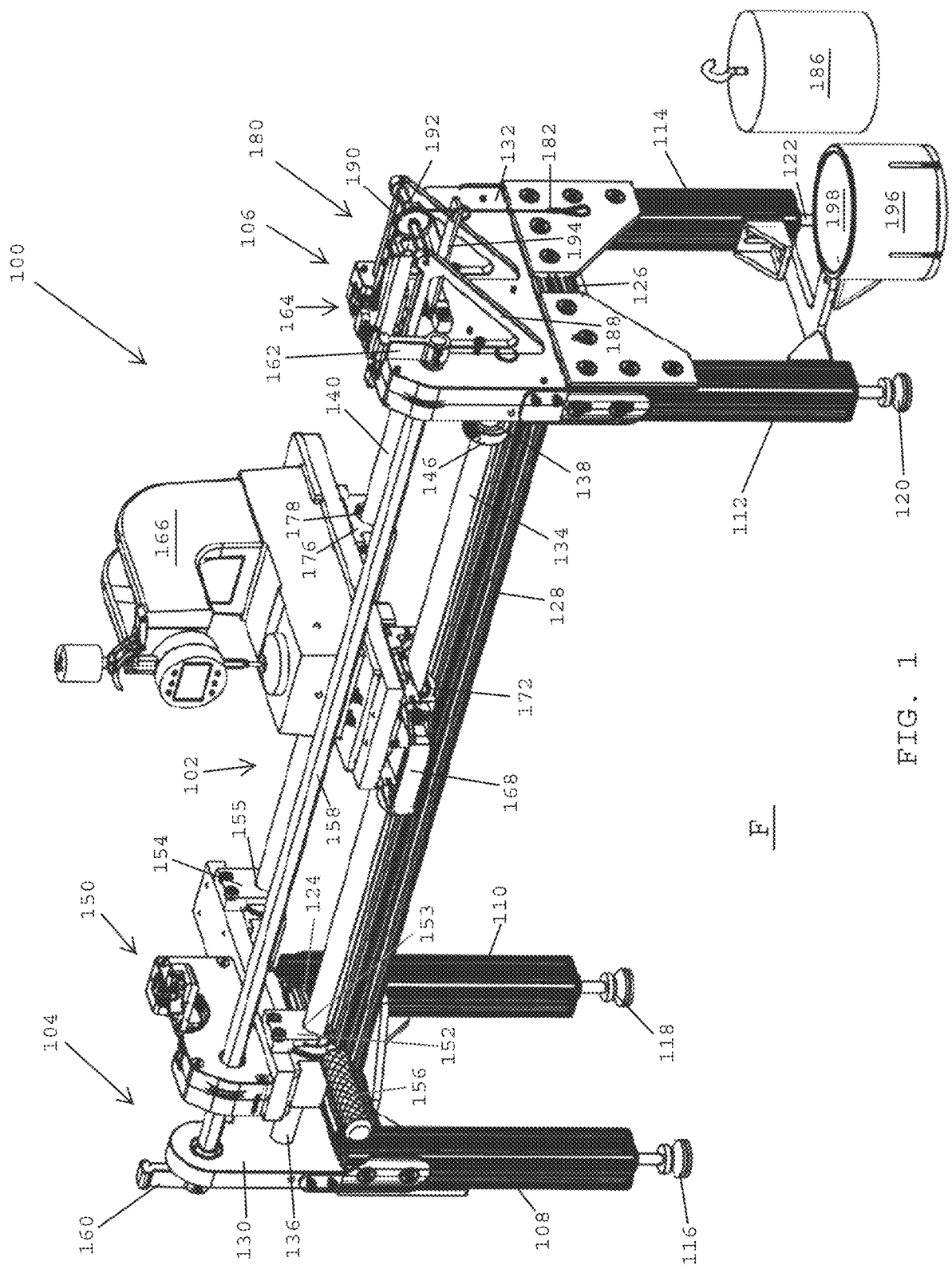
FIG. 1 is a perspective view of a system for measuring the diameters of sutures, in accordance with one embodiment of the present patent application.
Figure 2:
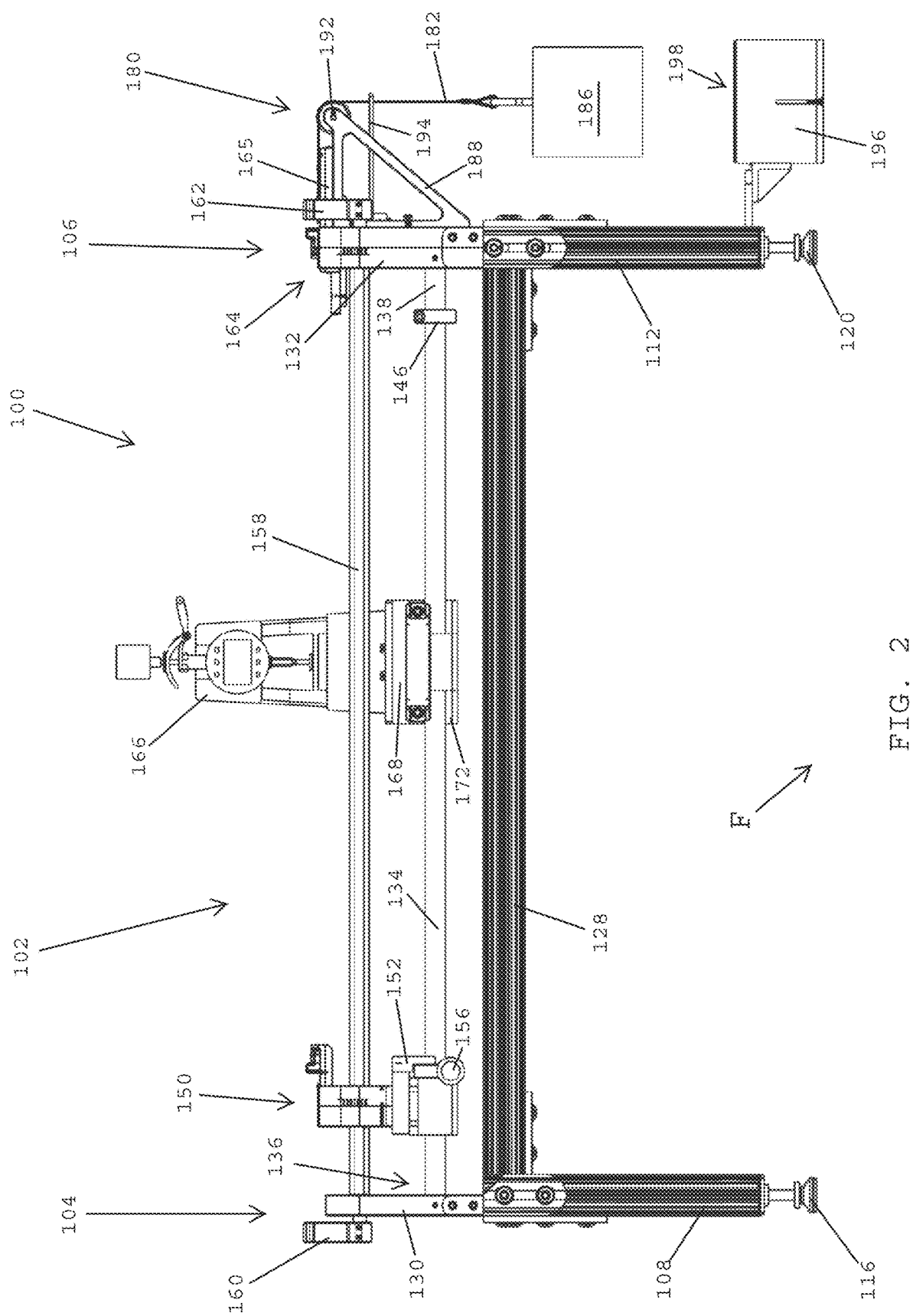
FIG. 2 is a front elevation view of the system shown in FIG. 1.
Figure 3:
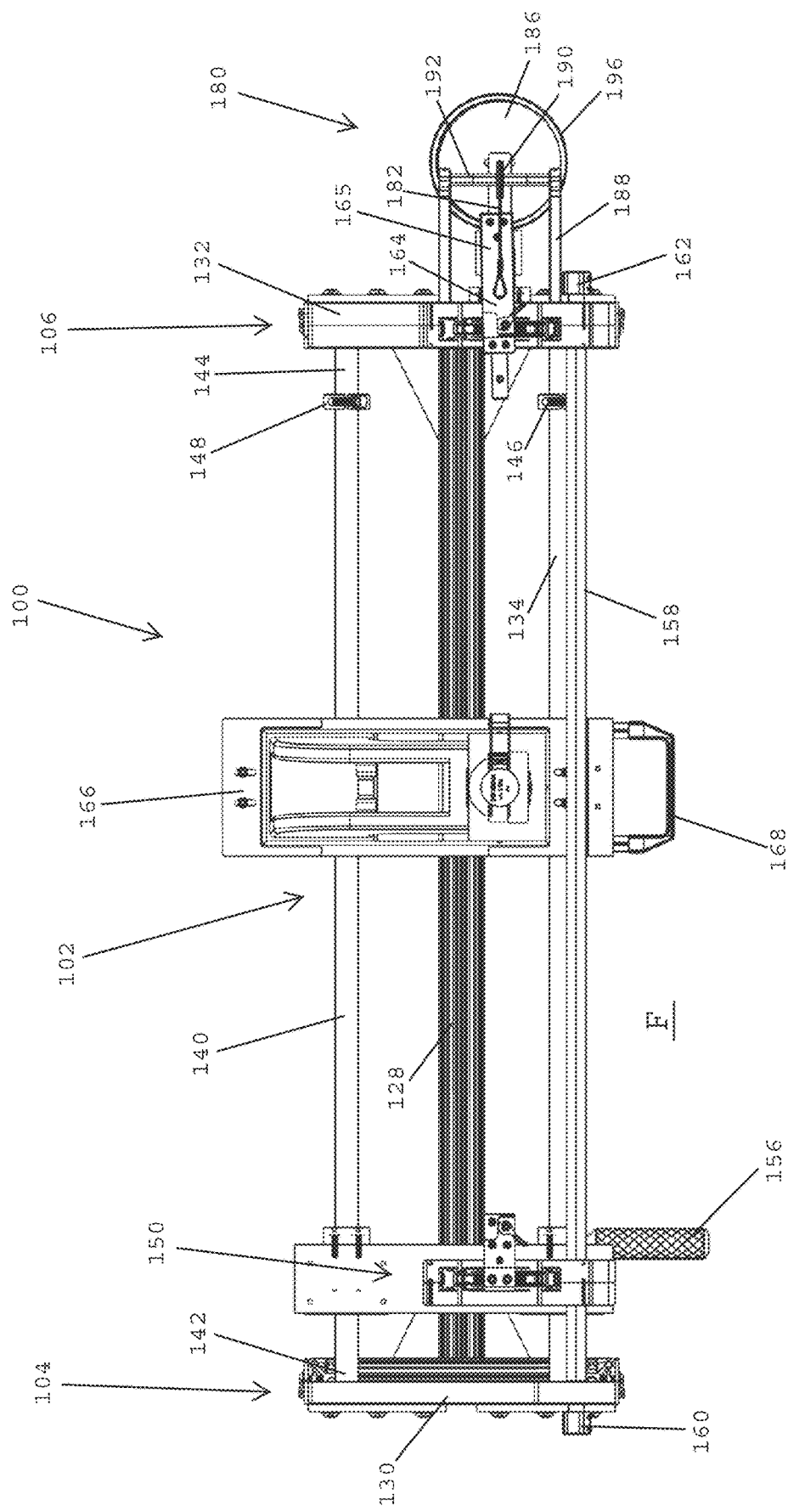
FIG. 3 is a top plan view of the system shown in FIG. 1.
Figure 4:
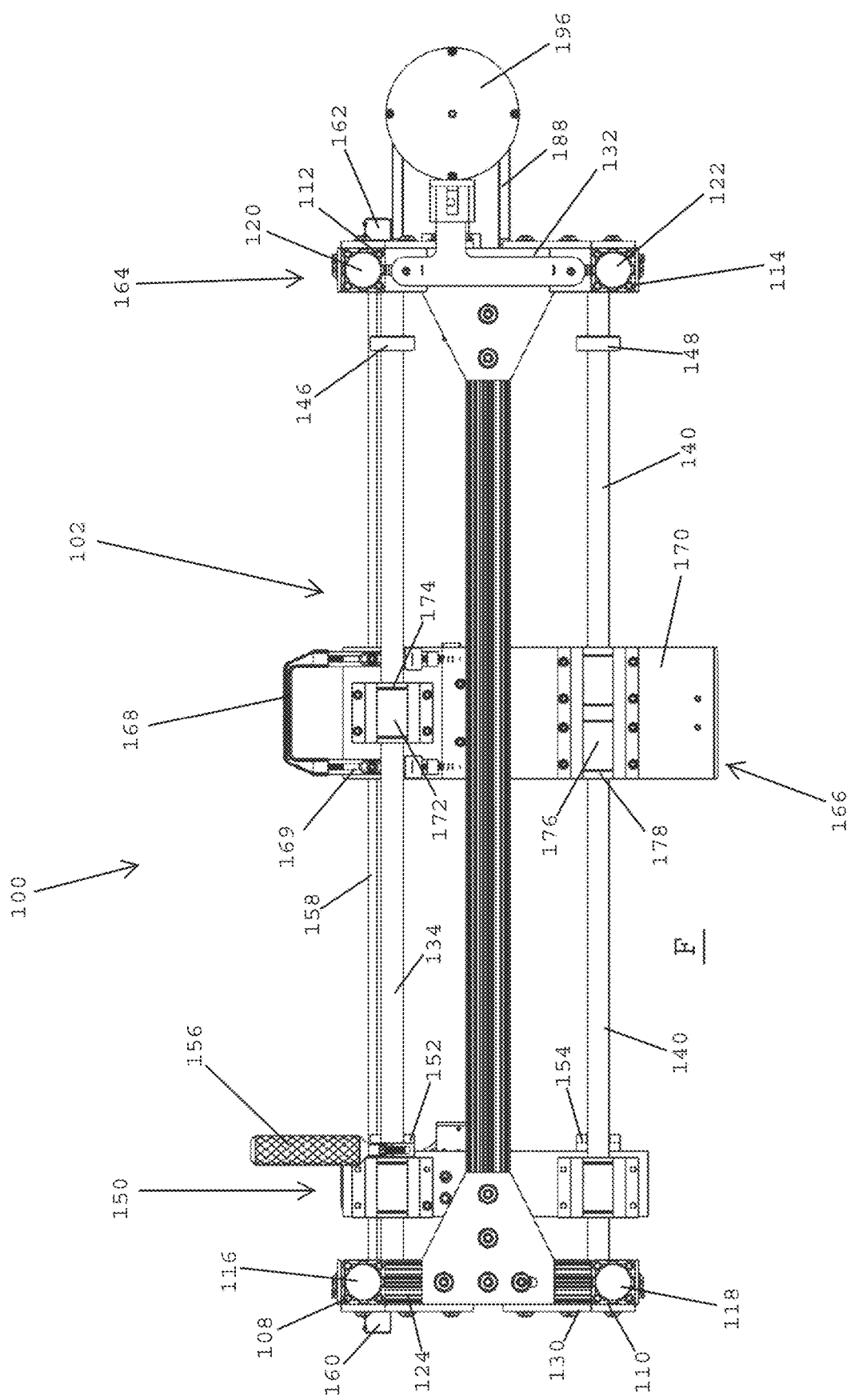
FIG. 4 is a bottom view of the system shown in FIG. 1.

Referring to FIGS. 1-4, in one embodiment, a system 100 for measuring the diameter of a suture preferably includes a test bench 102 having a left side 104 and a right side 106. In one embodiment, the test bench 102 preferably includes a left front leg 108 and a left rear leg 110, which are located on the left side 104 of the test bench 102, and a right front leg 112 and a right rear leg 114, which are located on the right side 106 of the test bench 102. In one embodiment, the four legs 108, 110, 112, and 114 of the test bench 102 preferably extend vertically above a floor surface F.

In one embodiment, the left front leg 108 preferably includes a leveling foot 116 for adjusting the height of the left front leg 108, and the left rear leg 110 preferably includes a leveling foot 118 for adjusting the height of the left rear leg 110. In one embodiment, the right front leg 112 desirably includes a leveling foot 120 for adjusting the height of the right front leg 112, and the right rear leg 114 includes a leveling foot 122 for adjusting the height of the right rear leg 114. In one embodiment, the leveling feet 116, 118, 120, and 122 may be adjusted up and down for leveling the test bench 102 over the floor surface F and/or adjusting the height of the test bench over the floor surface F.

In one embodiment, the test bench 102 desirably includes a left lateral support 124 that extends between the upper ends of the left front leg 108 and the left rear leg 110 for enhancing the structural integrity of the left side 104 of the test bench 102. The test bench 102 preferably includes a right lateral support 126 that desirably extends between the upper ends of the right front leg 112 and the right rear leg 114 for enhancing the structural integrity of the right side 106 of the test bench 102.

In one embodiment, the test bench 102 desirably includes a longitudinal support 128 that extends between the left lateral support 124 and a right lateral support 126 for further enhancing the structural integrity and strength of the test bench 102. In one embodiment, fastening elements and/or braces may be utilized in association with the vertical legs 108, 110, 112, and 114, the left and right lateral supports 124, 126, and the longitudinal support 128 for enhancing the structural integrity and strength of the test bench 102 to provide a stable test bench 102 and testing environment for measuring the diameters of sutures.

In one embodiment, the test bench 102 preferably includes a left end plate 130 that projects upwardly from the upper ends of the left front leg 108 and the left rear leg 110. The left end plate 130 is preferably stationary and does not move relative to the other components of the test bench 102.

In one embodiment, the test bench 102 desirably includes a right end plate assembly 132 including a right inner end plate and a right outer end plate that are assembled together. The right end plate assembly is preferably located at the right side 106 of the test bench 102. In one embodiment, the right end plate assembly 132 preferably projects upwardly from the upper ends of the respective right front leg 112 and right rear leg 114. The right end plate assembly is preferably stationary and does not move relative to the other components of the test bench 102.

In one embodiment, when measuring the diameters of sutures, one or more of the components of the test bench 102 are adapted to slide and/or move between the left side 104 and the right side 106 of the test bench 102. In order to facilitate the sliding movement of the one or more components, in one embodiment, the test bench 102 preferably includes a front guide rail 134 having a left side 136 that is secured to the left end plate 130 and a right side 138 that is secured to the right end plate assembly 132. In one embodiment, the front guide rail 134 may have a cylindrical-shaped cross-section and the sliding components may slide over the outer surface of the front guide rail 134. In one embodiment, the front guide rail 134 preferably couples the front sides of the respective left end plate 130 and the right end plate assembly 132, and desirably enhances the structural integrity of the test bench 102.

In one embodiment, the test bench 102 desirably includes a rear guide rail 140 having a left side 142 that is secured to the left end plate 130, and more preferably a left inner end plate, and a right side 144 that is secured to the right end plate assembly 132, and more preferably the right inner end plate. In one embodiment, the front and rear guide rails 134, 140 preferably extend along respective axes that are parallel to one another. The rear guide rail 140 preferably enables one or more slideable components of the test bench 102 to slide back and forth between the left side 104 and the right side 106 of the test bench 102. In one embodiment, the rear guide rail 140 preferably couples the rear sides of the respective left end plate 130 and right end plate assembly 132 for further enhancing the structural integrity of the test bench 102 and for supporting sliding components at the rear side of the test bench.

In one embodiment, the test bench 102 may include a front guide rail stop 146 that is secured over the front guide rail 134, and a rear guide rail stop 148 that is secured over the rear guide rail 140. As will be described in more detail herein, the front guide rail stop 146 and the rear guide rail stop 148 preferably control rightward sliding movement of a suture diameter gauge that is mounted on the guide rails 134, 140 and desirably prevents the suture diameter gauge from contacting the right end plate assembly 132 of the test bench 102, as will be described in more detail herein.

In one embodiment, the test bench 102 desirably includes a first suture clamping assembly 150 that is mounted upon the front guide rail 134 and the rear guide rail 140 for sliding back and forth between the left side 104 and the right side 106 of the test bench 102. The first suture clamping assembly 150 may be slid left and right for accommodating suture strands having different lengths. In one embodiment, the first suture clamping assembly 150 desirably includes a first guide collar 152 having an arcuate cutout 153 that is adapted to slide over the outer surface of the front guide rail 134 and a second guide collar 154 having an arcuate cutout 155 that is adapted to slide over the outer surface of the rear guide rail 140. In one embodiment, the first suture clamping assembly 150 desirably includes a locking handle 156 that is moveable between an unlocked position for enabling the first suture clamping assembly 150 to slide over the front and rear guide rails 134, 140, and a locked position that locks the first suture clamping assembly in place on the front and rear guide rails.

In one embodiment, when the first suture clamping assembly 150 has been moved to a desired position along the lengths of the respective front and rear guide rails 134, 140 (e.g., to accommodate a suture having a particular length), the locking handle 156 may be moved into the locked position for locking the first suture clamping assembly 150 in place and preventing any further left or right sliding movement of the first suture clamping assembly 150 relative to the front and rear guide rails 134, 140 of the test bench 102.

In one embodiment, the test bench 102 preferably includes a rotatable bar 158 that extends between the left end plate 130 and the right end plate assembly 132. In one embodiment, the rotatable bar 158 may be a hex bar having a hex-shaped cross section with six (6) sides. In one embodiment, the rotatable bar 158 may extend along the front side of the test bench 102. In one embodiment, the rotatable bar 158 desirably passes through aligned openings that are formed in the left end plate 130, the first suture clamping assembly 150, and the right end plate assembly 132. In one embodiment, a left side lever 160 is secured to the left end of the rotatable bar 158 and a right side lever 162 is secured to the right end of the rotatable bar 158. In one embodiment, the left and right side levers 160, 162 may be moved from a first position (e.g., a vertical orientation) that is associated with a zero degree position for the first suture clamping assembly 150, and a second position (e.g., a horizontal orientation) that is associated with a 90 degree position for the first suture clamping assembly 150, as will be described in more detail herein.

In one embodiment, the front side of the first suture clamping assembling 150 desirably includes an opening that receives the rotatable bar 158, whereby when the locking handle 156 is in the unlocked position the first suture clamping assembly 150 is free to slide left and right along the length of the rotatable bar 158 for positioning the first suture clamping assembly 150 at a preferred location between the left side 104 and the right side 106 of the test bench 102.

In one embodiment, the right end plate assembly 132 at the right side 106 of the test bench 102 desirably includes a second suture clamping assembly 164 provided thereon for clamping a second end of a suture for measuring the diameter of the suture. In one embodiment, a first end of a suture is secured to the first suture clamping assembly and a second end of the suture is secured to the second suture clamping assembly for measuring the diameter of the suture at various locations along the length of the suture.

In one embodiment, the second suture clamping assembly 164 extends upwardly from the right end plate assembly 132 and is fixed to the test bench 102. In one embodiment, the first suture clamping assembly 150 is adapted to slide between the left end plate 130 and the right end plate assembly 132 of the test bench 102 so that the distance between the first suture clamping assembly 150 and the second suture clamping assembly 164 may be adjusted for accommodating sutures having different lengths. For example, when measuring the diameter of a relatively longer suture, the first and second suture clamping assemblies are positioned further apart from one another, and when measuring the diameter of a relatively shorter suture, the first and second suture clamping assemblies are positioned closer together. In one embodiment, the second suture clamping assembly 164 is mounted atop a linear slide 165 (FIG. 3), which enables the suture to slightly stretch when a tensioning weight is applied to the linear slide.

In one embodiment, the test bench 102 desirably includes a suture diameter gauge 166 that is preferably adapted to measure the diameter of a suture which has a first end secured to the first suture clamping assembly 150 and a second end secured to the second suture clamping assembly 164. In one embodiment, the suture diameter gauge 166 is preferably adapted to slide over the front and rear guide rails 134, 140 for moving the suture diameter gauge 166 between the left end 104 and the right end 106 of the test bench 102. In one embodiment, after a suture has been secured to the first and second suture clamping assemblies, the suture diameter gauge is preferably used to measure the diameter of a suture at different locations along the length of the suture.

In one embodiment, the suture diameter gauge 166 desirably includes a suture diameter gauge handle 168 that may be grasped by an operator for moving the suture diameter gauge over the front and rear guide rails 134, 140, and positioning the suture diameter gauge 166 at selected locations along the lengths of the respective front and rear guide rails 134, 140. In one embodiment, the suture diameter gauge 166 preferably includes a brake assembly 169 that is coupled with the suture diameter gauge handle 168. When deployed, the brake assembly 169 prevents the suture diameter gauge 166 from sliding over the front and rear guide rails. In one embodiment, the brake assembly 169 may be moved into a first position in which the suture diameter gauge is free to slide over the front and rear guide rails 134, 140, and a second position (i.e., the braking position) in which the suture diameter gauge is locked in place on the front and rear guide rails 134, 140. In one embodiment, the brake assembly 169 may include a spring-loaded sliding joint, whereby when the suture diameter gauge handle 168 is pressed the brake assembly 169 is released and when the suture diameter gauge handle is released the brake is applied to halt sliding movement of the suture diameter gauge.

In one embodiment, the suture diameter gauge 166 may include a gauge base plate 170 that is adapted for facilitating sliding movement of the suture diameter gauge 166 over the respective front and rear guide rails 134, 140. In one embodiment, the suture diameter gauge 166 desirably includes a front bearing 172 that is secured to the underside of the gauge base plate 170. The front bearing 172 desirably includes an opening 174 that is adapted to receive the front guide rail 134 to facilitate sliding movement of the suture diameter gauge 166 over the front guide rail. In one embodiment, the suture diameter gauge 166 preferably includes a rear bearing 176 secured to the underside of the gauge base plate 170. The rear bearing 176 desirably includes a rear opening 178 that is adapted to receive the rear guide rail 140 for facilitating sliding movement of the suture diameter gauge 166 over the rear guide rail 140 of the test bench 102.

In one embodiment, the test bench 102 preferably includes a tensioning assembly 180 that is located at the right side 106 of the test bench 102 for tensioning a suture that is secured to the second suture clamping assembly 164. In one embodiment, the tensioning assembly 180 preferably includes a tensioning cable 182 having an upper end secured to the linear slide 165 and a lower end secured to a tensioning weight 186. The linear slide 165 is preferably connected with the second suture clamping assembly 164 for applying tension to an end of a suture secured to the second suture clamping assembly. The tensioning assembly 180 desirably includes a pulley bracket 188 having a spindle 190 that supports a rotatable pulley 192 that receives the tensioning cable 182. In one embodiment, the tensioning assembly 180 desirably includes a tensioning cable aligner 194 that controls and/or limits swinging movement of the tensioning cable 182 as tension is applied to the linear slide 165 via the tensioning cable 182.

In one embodiment, the tensioning assembly 180 preferably includes a tensioning weight catch 196 that has an opening 198 at an upper end thereof adapted to receive the tensioning weight 186. When not in use, the tensioning weight 186 may be stored in the tensioning weight catch 196.

Figure 5:
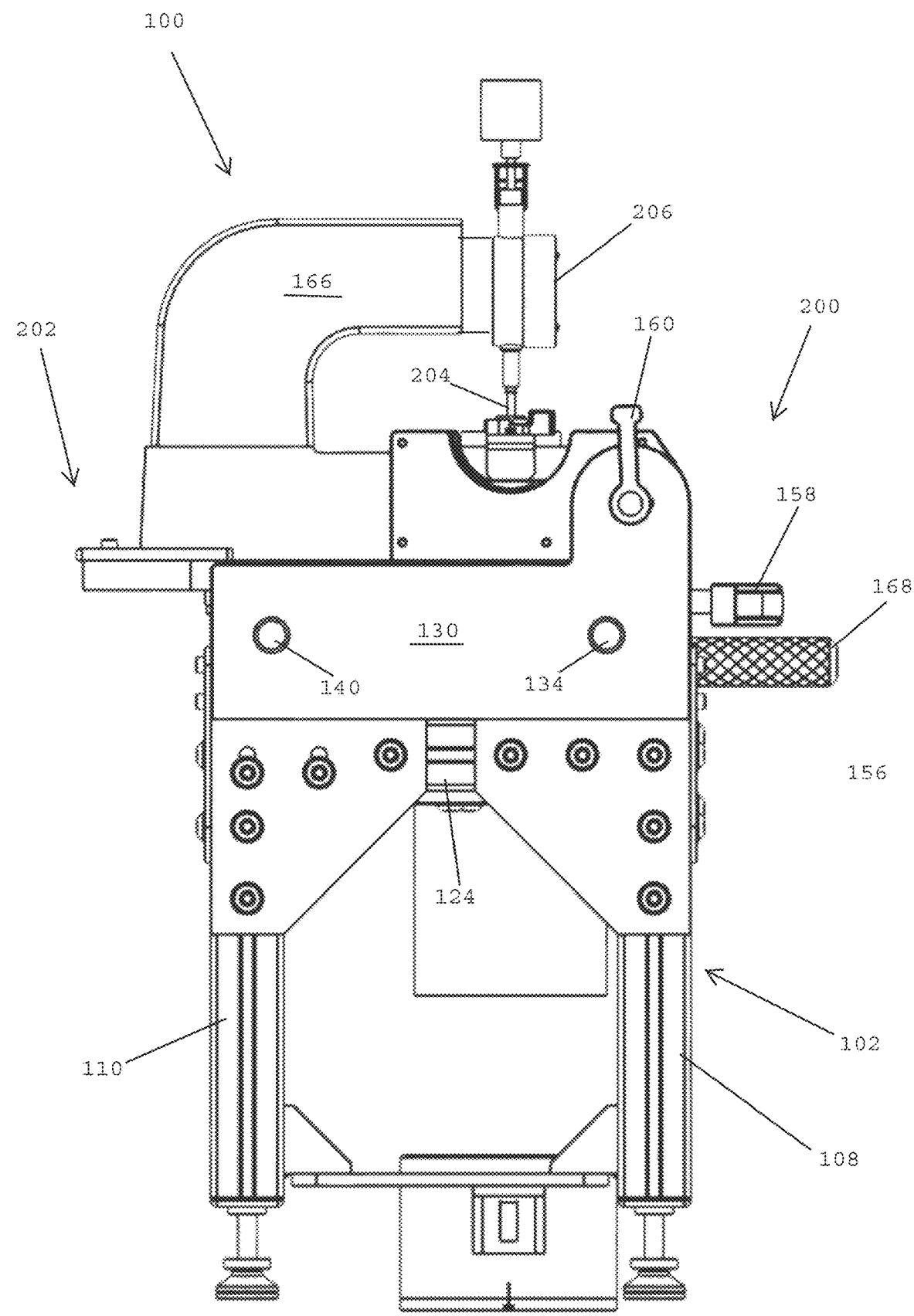
FIG. 5 is a left side view of the system shown in FIG. 1.

Referring to FIG. 5, in one embodiment, the test bench 102 for measuring the diameter of sutures preferably has a front side 200 and a rear side 202. In one embodiment, an operator may be located at the front side 200 for measuring the diameters of sutures. The left front leg 108 preferably extends vertically along the front side 200 of the test bench 102 and the left rear leg 110 preferably extends vertically along the rear side 202 of the test bench 102. The left lateral support 124 desirably interconnects the upper ends of the left front leg 108 and the left rear leg 110 for enhancing the structural integrity of the test bench 102. The test bench 102 desirably includes the front guide rail 134 and the rear guide rail 140 secured to the left end plate 130. The test bench 102 desirably includes the rotatable bar 158 that passes through an opening in the left end plate 130 for being coupled with a left lever 160 that is utilized for rotating the first and second suture clamping assemblies 150, 164 (FIG. 1) between the zero degree position and the 90 degree position.

The test bench 102 preferably includes the suture diameter gauge 166 that is coupled with the front and rear guide rails 134, 140 for sliding between the left and right sides of the test bench. The suture diameter gauge 166 desirably includes a test probe 204 that is configured to be lowered onto a suture that is aligned with the test probe for measuring the diameter of the suture, and a digital display 206 that preferably shows the diameter of the suture that has been measured by the test probe 204.

In one embodiment, the locking handle 156 is preferably accessible at the front side 200 of the work bench 102 for selectively sliding and positioning the first suture clamping assembly 150 (FIG. 1) at different locations along the lengths of the respective front and rear guide rails 134, 140. The distance between the first and second suture clamping assemblies may be adjusted for accommodating sutures having different lengths.

In one embodiment, the suture diameter gauge 166 desirably includes the gauge handle 168 that may be grasped by an operator located at the front side 200 of the test bench 102 for adjusting the lateral position of the suture diameter gauge 166 between the left and right sides 104, 106 of the test bench 102 and along the lengths of the respective front and rear guide rails 134, 140. In one embodiment, the suture diameter gauge may include the brake assembly 169 (FIG. 4) for locking the suture diameter gauge in place at a particular point or location along the lengths of the respective front and rear guide rails.

Figure 6:
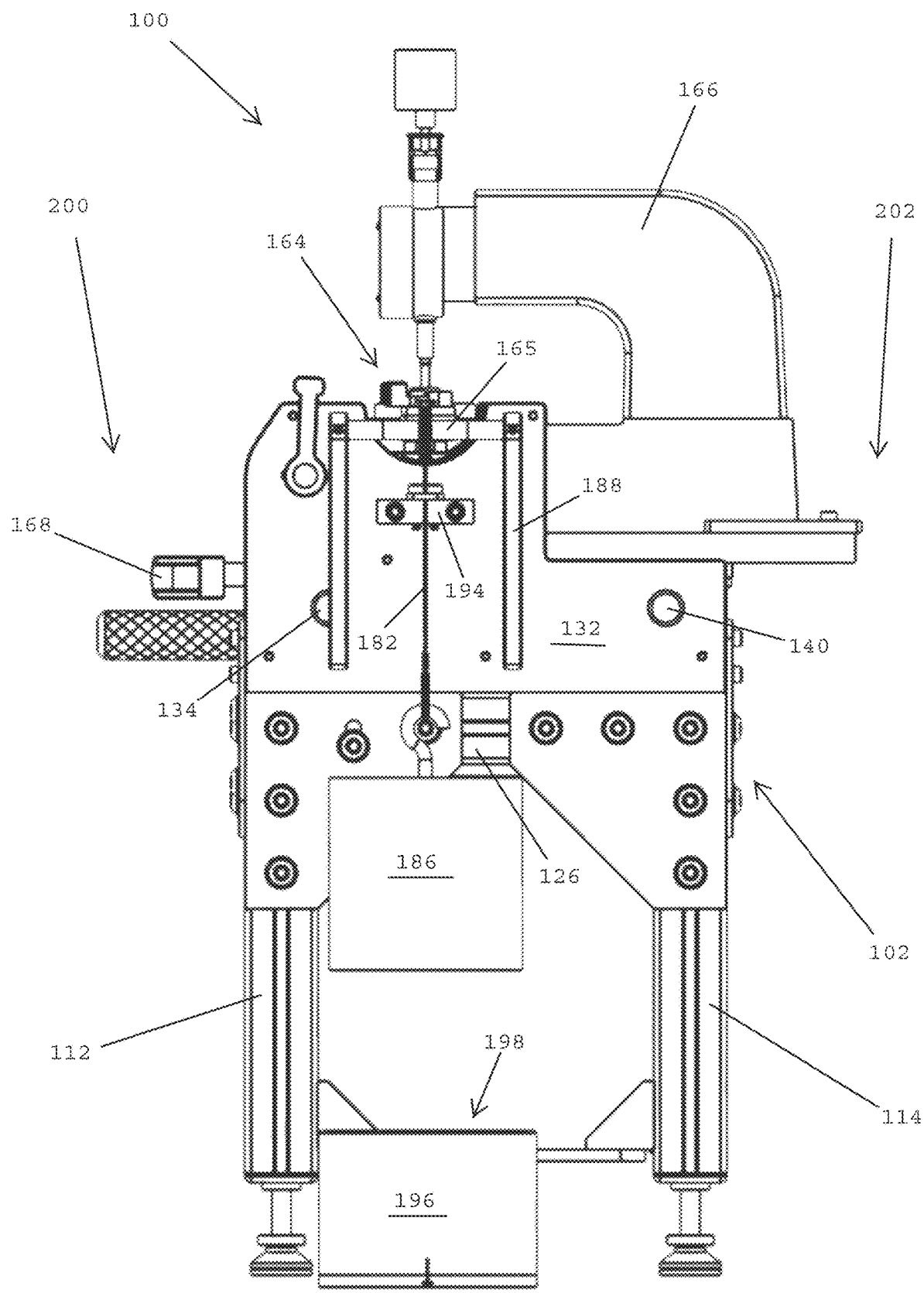
FIG. 6 is a right side view of the system shown in FIG. 1.

Referring to FIG. 6, in one embodiment, the test bench 102 preferably includes the right front leg 112 and the right rear leg 114 having upper ends coupled with the right lateral support 126 for stabilizing the right side 106 of the test bench 102 (FIG. 1). The test bench 102 preferably includes the right end plate assembly 132 that projects upwardly from the upper ends of the respective right front leg 112 and right rear leg 114. The second suture clamping assembly 164 is located at the upper end of the right end plate assembly 132.

In one embodiment, the right ends of the respective front and rear guide rails 134, 140 are desirably secured to the right end plate assembly 132 (e.g., the right inner end plate) for enhancing the structural integrity of the right side of the test bench 102. The right side of the test bench 102 preferably includes the tensioning assembly 180 having the tensioning cable 182 with an upper end secured to a linear slide 165 and a lower end coupled with a tensioning weight 186. The tensioning assembly 180 is preferably adapted to provide tension to the second suture clamping assembly 164 to apply tension to a suture having an end that is secured to the second suture clamping assembly 164.

In one embodiment, the tensioning assembly 180 desirably includes the pulley bracket 188 that may be secured to the right outer end plate of the right end plate assembly 132. The tensioning assembly 180 may also include the tensioning cable aligner 194 that guides and aligns the tensioning cable 182 to prevent any undesirable swinging of the lower end of the tensioning cable 182 and/or the tensioning weight 186. The tensioning weight catch 196 has an opening 198 at an upper end thereof that is adapted to receive the tensioning weight 186, such as when the tensioning weight is not in use and is being stored inside the tensioning weight catch.

In one embodiment, the suture diameter gauge 166 is preferably mounted upon the front and rear guide rails 134, 140 for selectively sliding the suture diameter gauge between the left and right sides of the test bench 102. The gauge handle 168 may be grasped from the front side 200 of the test bench 102 for selectively moving the suture diameter gauge 166 along the length of the front and rear guide rails 134, 140.

Figure 7:
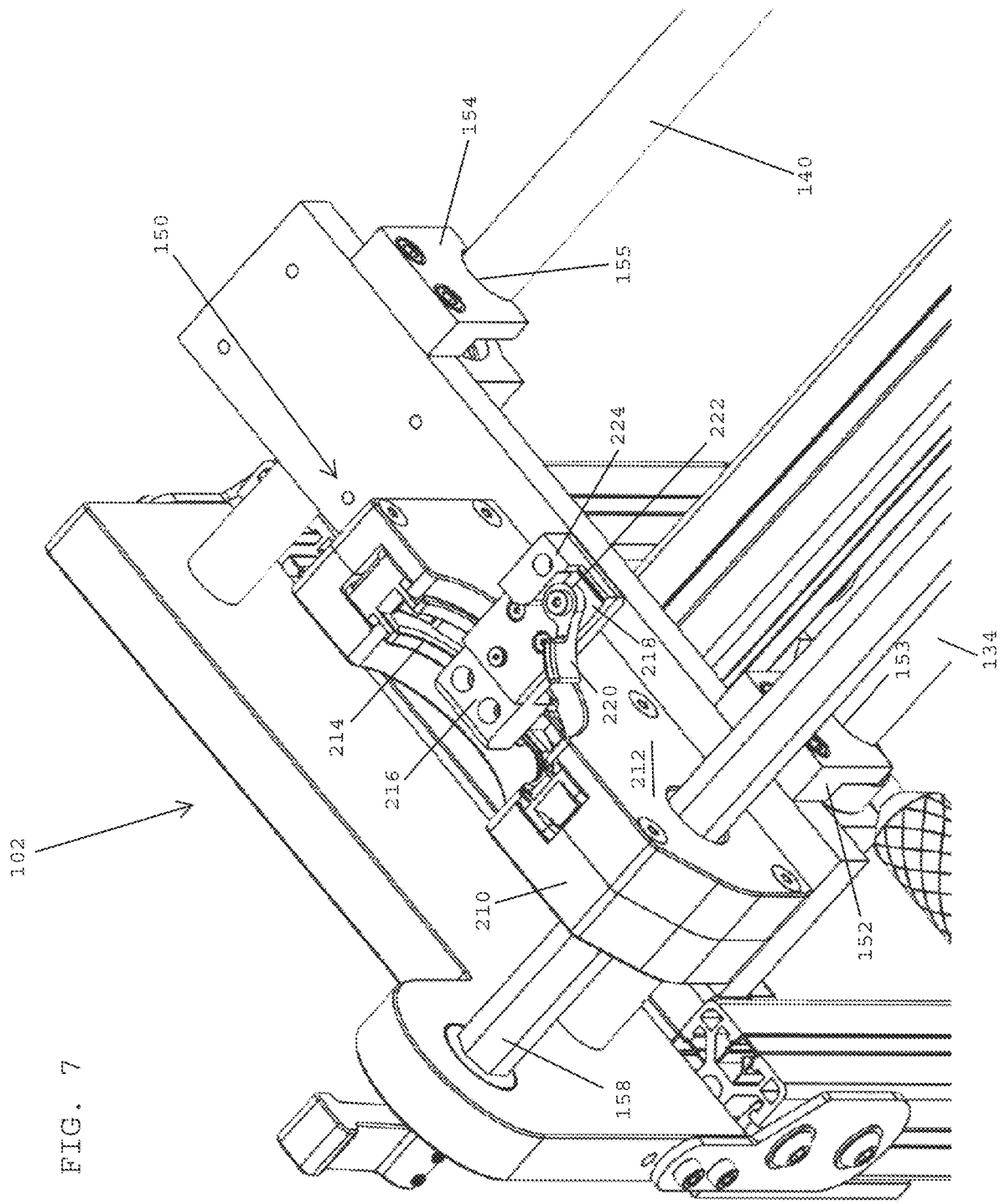
FIG. 7 is a perspective view of a left side of the system shown in FIG. 1 including a first suture clamping assembly, in accordance with one embodiment of the present patent application.

Referring to FIG. 7, in one embodiment, the first suture clamping assembly 150 is preferably adapted to slide over the front and rear guide rails 134, 140 for selectively positioning the first suture clamping assembly at desired locations between the left and right sides of the test bench 102. In one embodiment, the first suture clamping assembly 150 desirably includes a front collar 152 having an arcuate shaped underside 153 that is adapted to slide over the outer surface of the front guide rail 134 and a rear collar 154 having an arcuate underside 155 that is adapted to slide over the outer surface of the rear guide rail 140.

In one embodiment, the first suture clamping assembly 150 preferably includes a first outer gear plate 210 and a first inner gear plate 212 that are adapted to receive a first large gear 214 that may move relative to the first outer and inner gear plates 210, 212. In one embodiment, the first outer and inner gear plates 210, 212 preferably have aligned openings that are adapted to receive the rotatable bar 158 so that the first outer and inner gear plates 210, 212 may slide along the length of the rotatable bar 158 for adjusting the distance between the first suture clamping assembly 150 and the second suture clamping assembly 164 (FIG. 1).

In one embodiment, the first suture clamping assembly 150 desirably includes a first suture mount 216 that is secured to the first large gear 214 and that is adapted to rotate simultaneously with the first large gear 214 as the first large gear moves between two positions such as the zero degree position and the 90 degree position. The first suture mount 216 desirably includes a first suture mounting surface 218 that is adapted to seat a first end of a suture for securing the first end of the suture to the first suture clamping assembly 150. In one embodiment, the first suture mount 216 preferably includes a first suture securing lever 220 having a first cam surface 222 that opposes a first suture backstop 224. In one embodiment, a first end of a suture may be positioned between the first cam surface 222 and the first suture backstop 224, whereupon the first suture lever 220 may be moved into a locked position for securing the first end of the suture between the first cam surface 222 and the first suture backstop 224. Once the first end of the suture is secured to the first suture mount 216, the suture may be rotated simultaneously with the first suture mount 216 between the zero degree position and the 90 degree position for measuring the diameter of the suture at both the zero degree position and the 90 degree position. Thus, the diameter of a suture can be measured twice at the same point along the length of a suture with the first diameter measurement being at a right angle to the second diameter measurement. In one embodiment, a suture may be secured to the first suture clamping assembly by tying a loop or a knot of the suture around a post and passing the suture through an alignment notch that aligns the secured suture with the axis of rotation and the measurement plane of the suture diameter gauge.

Figure 8:
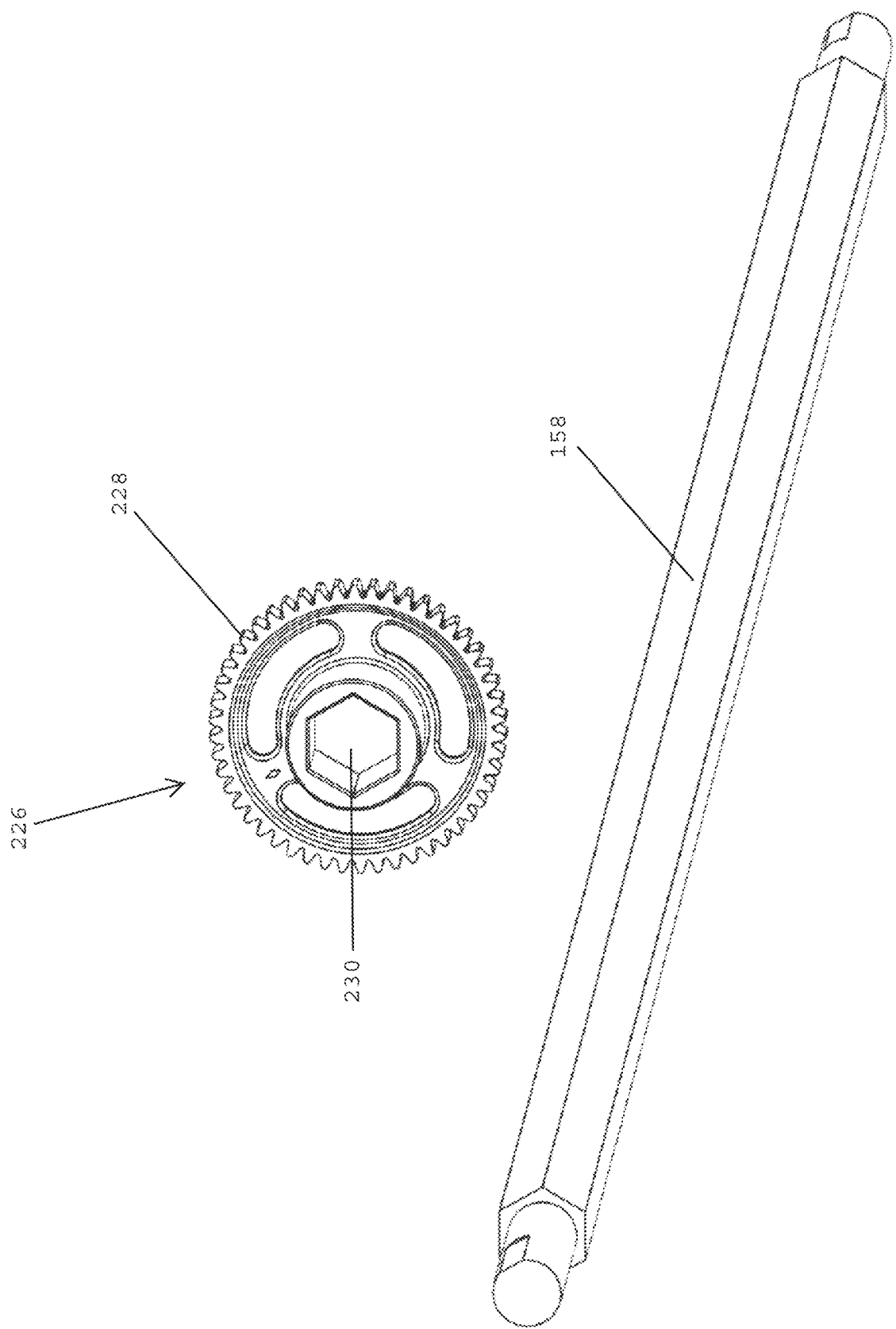
FIG. 8 is a perspective view of a rotatable bar and a first small gear that is mounted on the rotatable bar, in accordance with one embodiment of the present patent application.

Referring to FIG. 8, in one embodiment, the rotatable bar 158 is preferably adapted to receive a first small gear 226 that may be secured over an outer surface of the rotatable bar. In one embodiment, the first small gear 226 has gear teeth 228 and includes a central opening 230 having a shape that matches the shape (e.g., a hex shape) of the outer surface of the rotatable bar 158. The rotatable bar 158 may have different cross-sectional shapes and structures including but not limited to hex shaped bars, bars having keyed shafts, and bars having splined shafts. In one embodiment, when the first small gear 226 is mounted on the rotatable bar 158, rotation of the rotatable bar 158 will result in simultaneous rotation of the first small gear.

Figure 9:
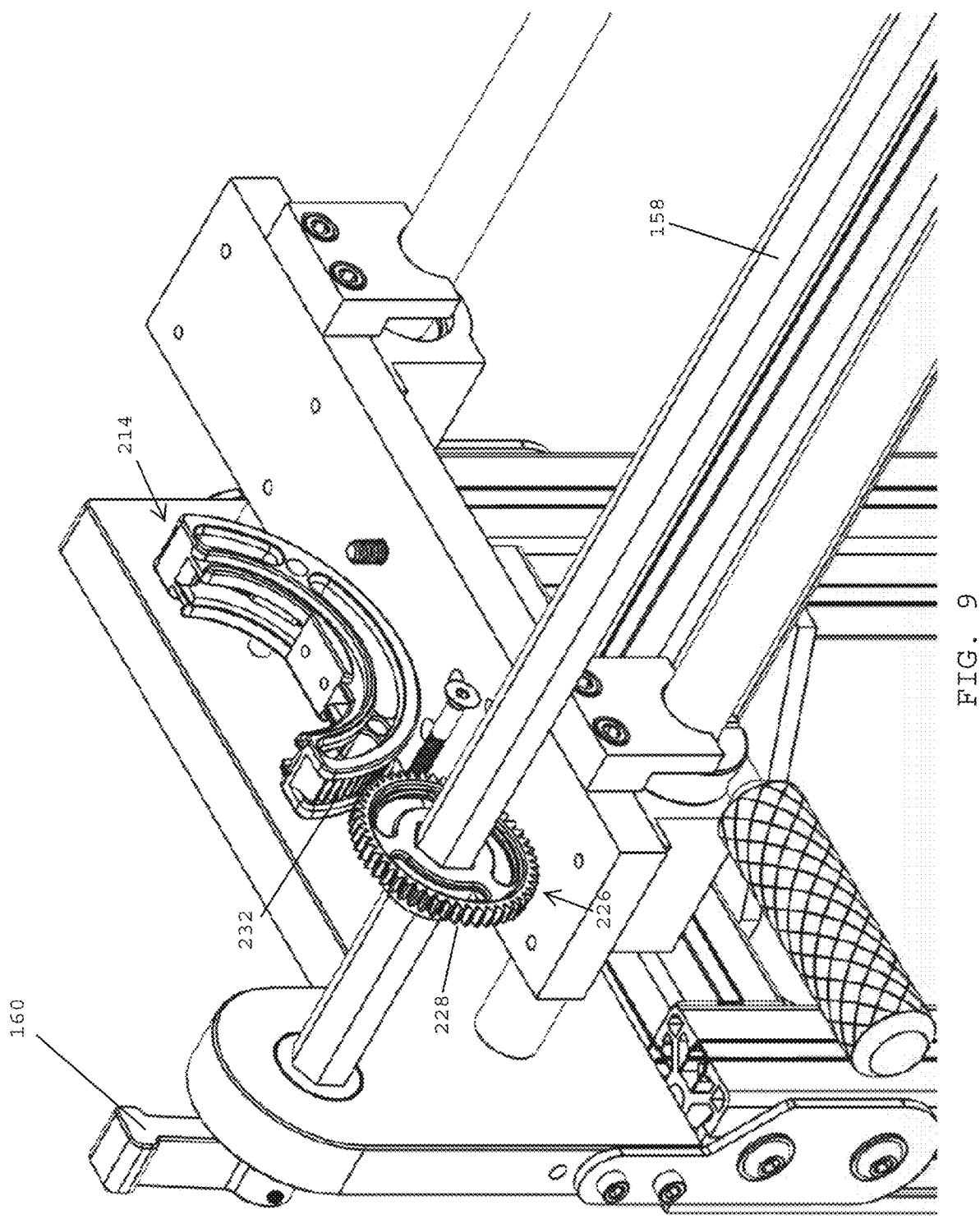
FIG. 9 is a partially exploded view of a left side of the system shown in FIG. 1 including the rotatable bar and the first small gear of FIG. 8 and a first large gear that meshes with the first small gear, in accordance with one embodiment of the present patent application.

Referring to FIG. 9, in one embodiment, the first small gear 226 is preferably mounted on the rotatable bar 158. The first small gear 226 has outer teeth 228 that mesh with outer teeth 232 that are provided on a convexly curved outer side surface of the first large gear 214. The left lever 160, which is secured to the left end of the rotatable bar 158, is rotatable from a first orientation shown in FIG. 9 to a second orientation for rotating the rotatable bar 158, which, in turn, rotates the first small gear 226 in a counterclockwise direction, which, in turn, rotates the first large gear 214 in a clockwise direction from the zero degree position shown in FIG. 9 to a 90 degree position shown in FIG. 24A. As the first small gear 226 rotates in the counterclockwise direction, the gear teeth 228 of the first small gear 226 preferably engage the gear teeth 232 of the first large gear 214 for rotating the first large gear in the clockwise direction. In one embodiment, due to the gear ratio between the first small gear 226 and the first large gear 214, the rotatable bar may be rotated about 180 degrees for rotating the first large gear about 90 degrees.

Referring to FIGS. 10A and 10B, in one embodiment, the first large gear 214 preferably has the shape of a half circle. In one embodiment, the first large gear 214 desirably has a convexly curved outer surface 234 having gear teeth 232 that are adapted to mesh with the gear teeth of the first small gear 226 (FIG. 9). The first large gear 214 preferably has a concave curved inner surface with a centrally located mounting platform 236 that is adapted to seat the first suture mount 216 (FIG. 7). In one embodiment, the lateral sides of the first large gear 214 have respective curved guide flanges 237A, 237B that define respective curved grooves 239A, 239B that are adapted to receive curved retaining lips on the first outer and inner gear plates 210, 212 (FIG. 7) for enabling the first large gear to rotate relative to the gear plates.

Referring to FIG. 10B, in one embodiment, the first large gear 214 is a half circle and has a diameter D that intersects with a center C of the circle. In one embodiment, when an end of a suture S is secured to the first suture clamping assembly 150 (FIG. 1), the suture S is preferably aligned with the center C and is held in the center C as the first large gear 214 rotates between the first zero degree position and the second 90 degree position. In one embodiment, the first and second suture clamping assemblies 150, 164 (FIG. 1) preferably hold the suture S taut so that it remains aligned within the center C as the suture S is rotated from the first zero degree position to the second 90 degree position.

Figure 11:
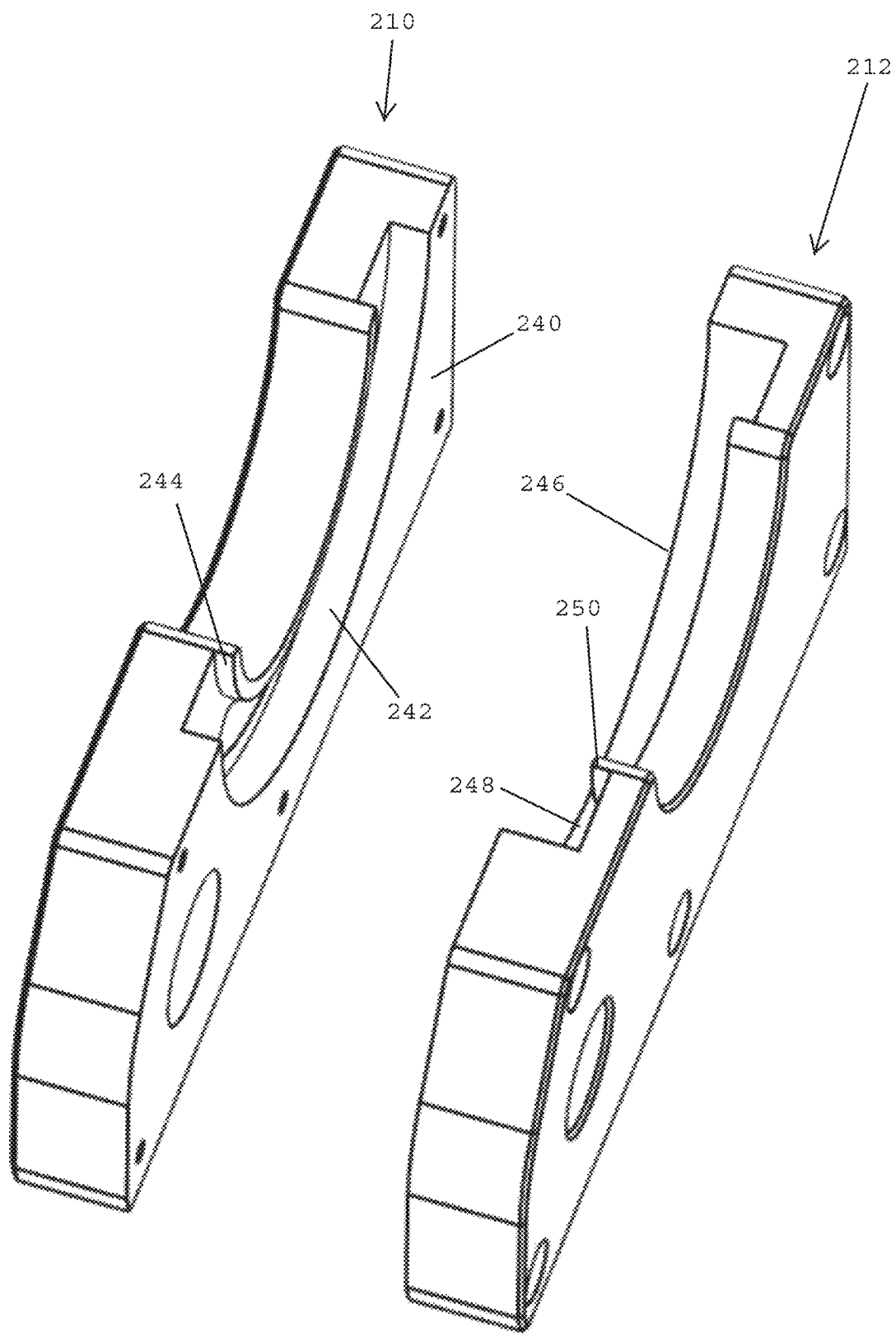
FIG. 11 shows an exploded view of first outer and inner gear plates that are used for securing the first large gear of FIGS. 10A and 10B, in accordance with one embodiment of the present patent application.

Referring to FIG. 11, in one embodiment, the first outer and inner gear plates 210, 212 are preferably secured together for holding the first large gear 214 (FIGS. 10A and 10B) between the gear plates, whereupon the first large gear may be selectively rotated relative to the gear plates. In one embodiment, the first outer gear plate 210 preferably has an inner face 240 having a first large gear groove 242 formed therein that conforms to the shape of the large gear 214 (FIG. 10B). The first outer gear plate 210 preferably includes a first curved retaining lip 244 that extends along the upper end of the first large gear groove 242. The first curved retaining lip 244 preferably sits in the first curved groove 239A (FIG. 10A) of the first large gear for restraining the first large gear as the first large gear moves between the zero degree position and the 90 degree position.

The first inner gear plate 212 preferably includes an inner face 246 having a second large gear groove 248 formed therein that conforms to the shape of the first large gear and that is adapted to seat the first large gear as it moves between the zero degree position and the 90 degree position. The first inner gear plate 212 preferably includes a second curved retaining lip 250 that is located at the upper end of the second large gear groove 248. The second curved retaining lip 250 preferably sits in the second curved groove 239B (FIGS. 10A and 10B) of the first large gear for restraining the first large gear as the first large gear moves between the zero degree position and the 90 degree position.

Figure 12:
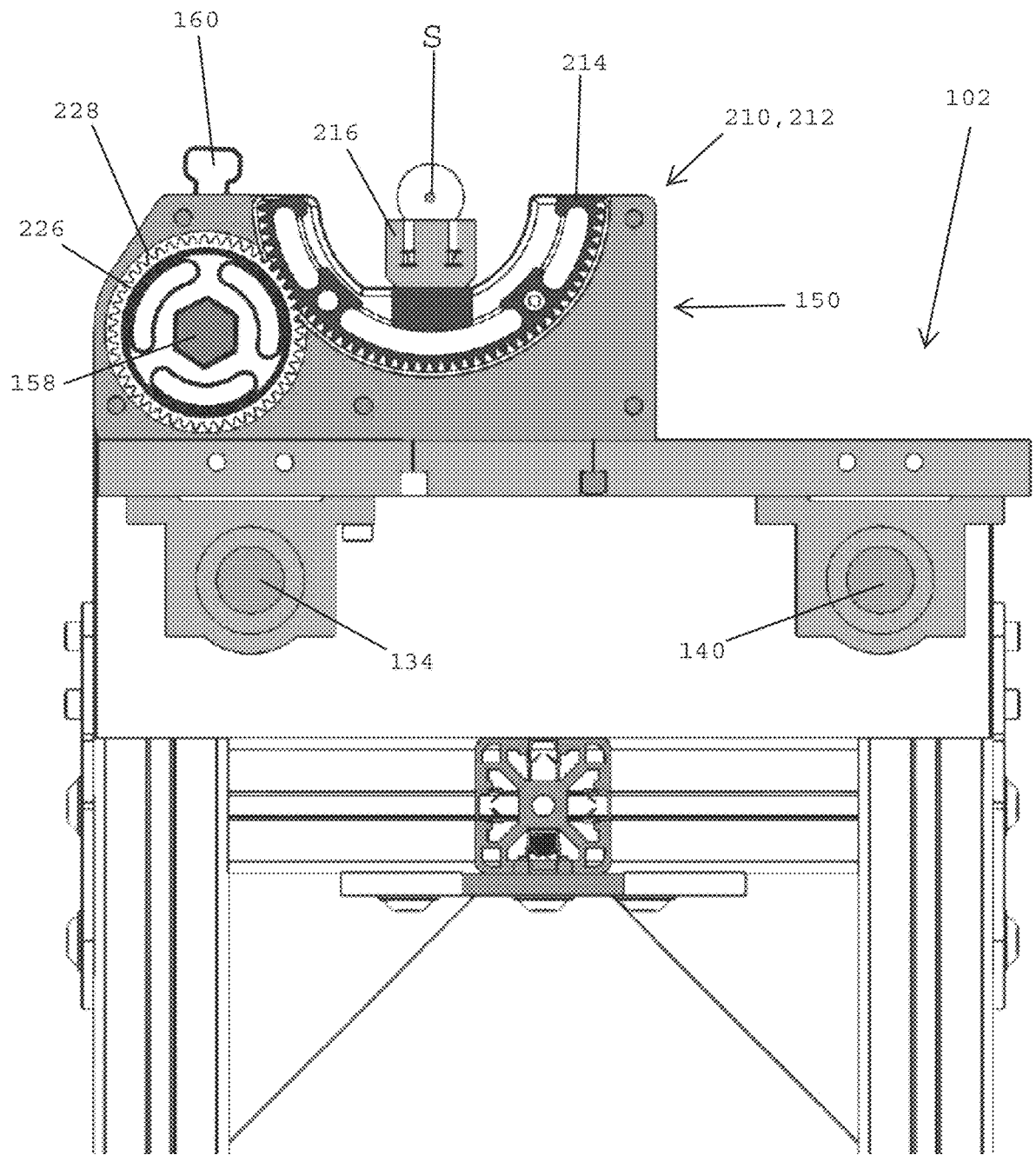
FIG. 12 shows a cross-sectional view of the system shown in FIG. 1 including the rotatable bar and the first small gear of FIG. 9 and the first large gear of FIGS. 10A and 10B meshing with the first small gear, in accordance with one embodiment of the present patent application.

Referring to FIG. 12, in one embodiment, the first suture clamping assembling 150 is coupled with the front guide rail 134 and the rear guide rail 140, and is adapted to slide along the front and rear guide rails 134, 140 for positioning the first suture clamping assembly 150 at selected locations between the left and right ends of the test bench 102. In one embodiment, the first suture clamping assembly 150 preferably includes the first large gear 214 that is mounted between the first outer and inner gear plates 210, 212. In one embodiment, the first suture clamping assembly 150 preferably includes the first small gear 226 that is mounted on the rotatable bar 158 and that is also positioned between the first outer and inner gear plates 210, 212. The gear teeth 228 of the first small gear 226 preferably mesh with the gear teeth 232 of the first large gear 214. The left lever 160, which is coupled with the rotatable bar 158, may be moved for rotating the first small gear 226, which, in turn, will rotate the first large gear 214 between the zero degree position and the 90 degree position. As the first large gear 214 rotates between the zero degree position and the 90 degree position, the suture mount 216, which is secured to the first large gear, preferably rotates simultaneously with the first large gear 214 so that the suture S secured over the suture mounting surface 218 (FIG. 7) of the suture mount 216 will also rotate on its axis between the zero degree position and the 90 degree position.

Figure 13:
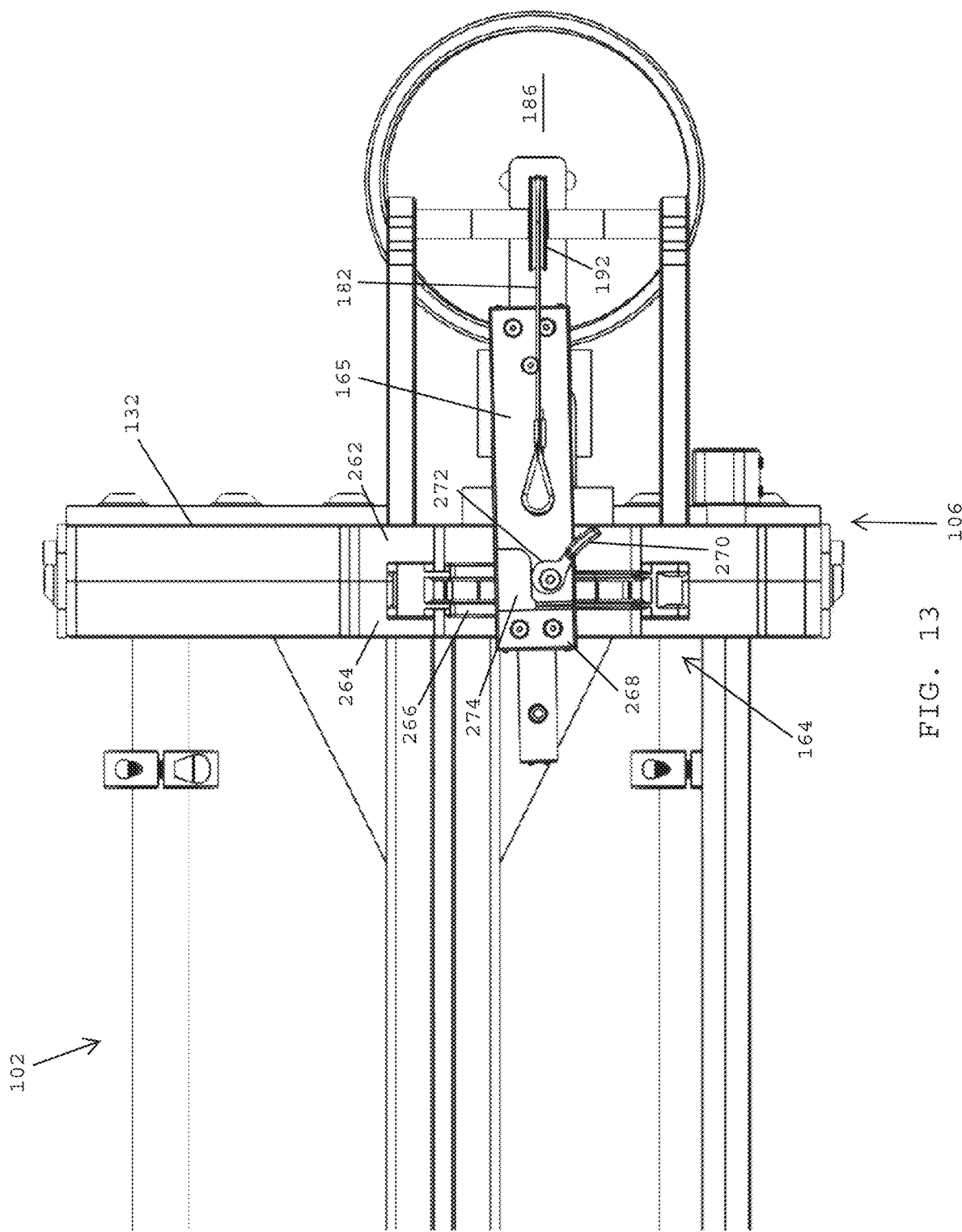
FIG. 13 shows a top plan view of a right side of the system shown in FIG. 1 including a second suture clamping assembly, in accordance with one embodiment of the present application.
Figure 14:
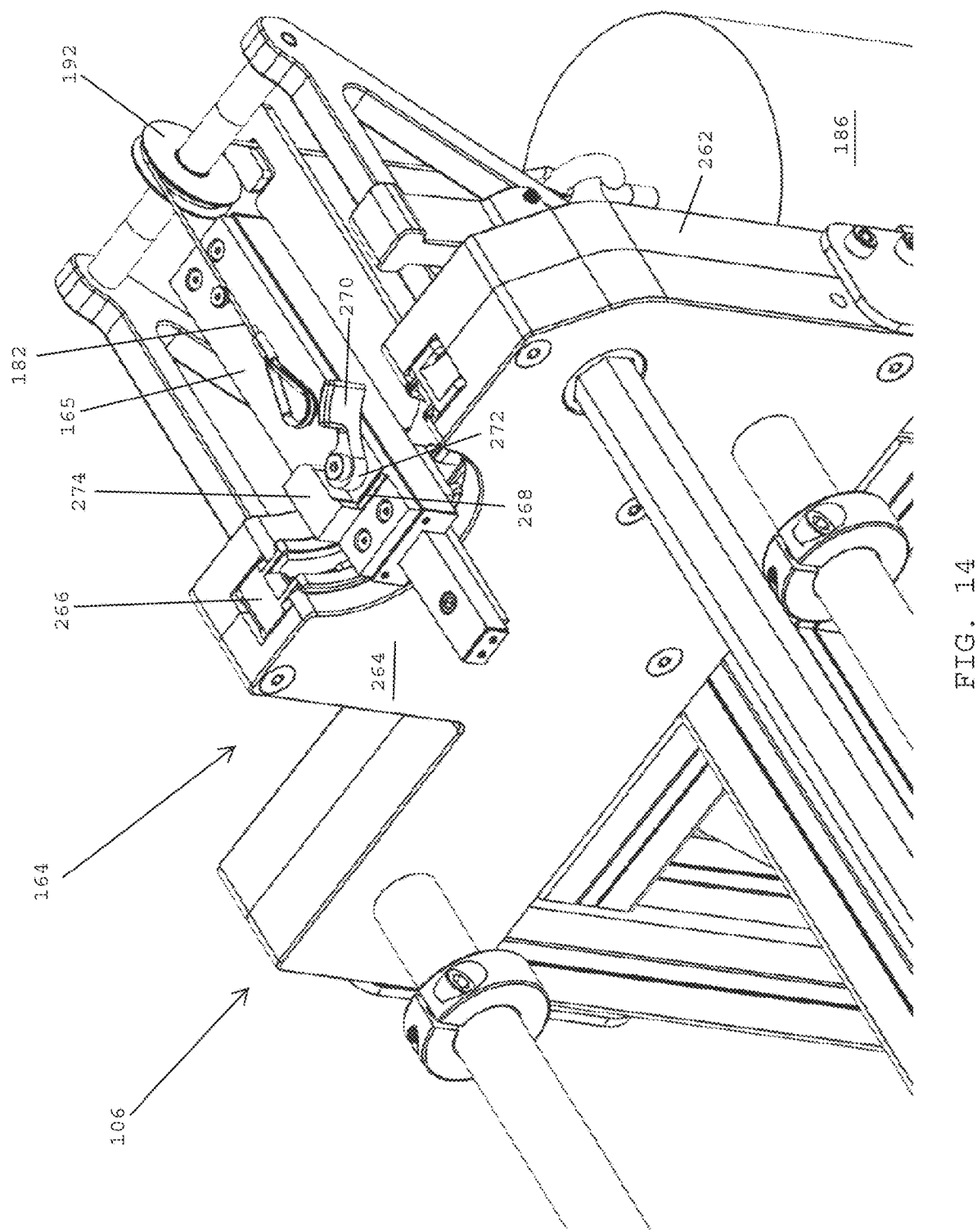
FIG. 14 shows a perspective view of the second suture clamping assembly of FIG. 13.
Figure 15:
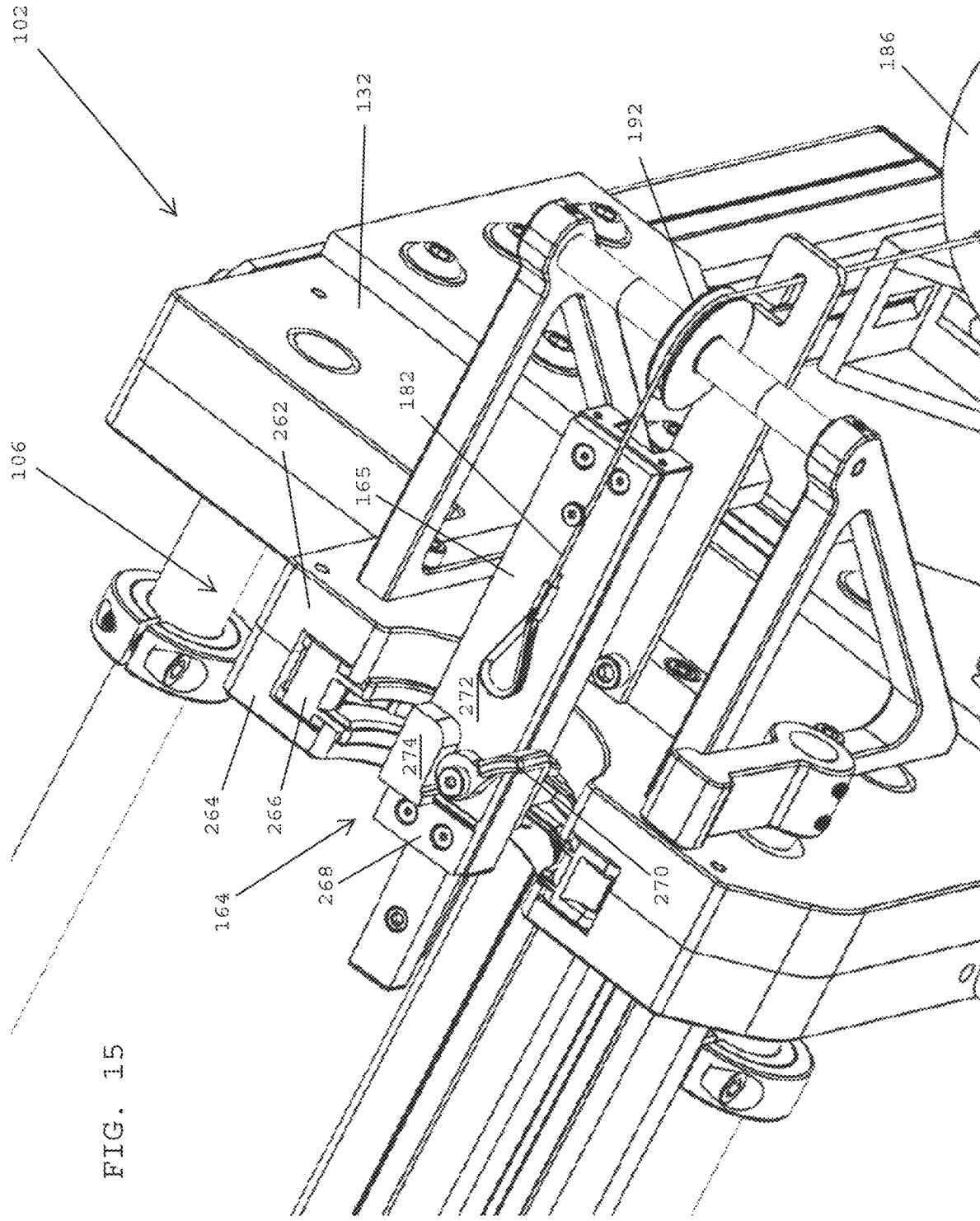
FIG. 15 shows another perspective view of the second suture clamping assembly of FIGS. 13 and 14.

Referring to FIGS. 13-15, in one embodiment, the right side 106 of the test bench preferably includes the second suture clamping assembly 164 (FIG. 1) that is adapted to secure a second end of a suture for measuring the diameter of the suture. In one embodiment, the second suture clamping assembly has a generally similar structure and/or similar components as the first suture clamping assembly described herein. In one embodiment, the second suture clamping assembly 164 preferably includes a second outer gear plate 262 and a second inner gear plate 264 that project above the right end plate assembly 132. In one embodiment, the second suture clamping assembly 164 preferably includes a second large gear 266 that is positioned between the second outer and inner gear plates 262, 264. The second large gear 266 is adapted to rotate between a zero degree position and a 90 degree position for rotating a suture that is secured to the second suture clamping assembly. In one embodiment, the first and second suture clamping assemblies 150 (FIG. 1), 164 are linked to one another via the rotatable bar 158 for simultaneously rotating the first and second suture clamping assemblies together between the zero degree position and the 90 degree position.

In one embodiment, the second suture clamping assembly 164 preferably includes a second suture mount 268 that is adapted to seat an end of a suture. The second suture mount 268 preferably includes a second locking lever 270 having a second cam surface 272 and an opposing second suture backstop 274. In one embodiment, a second end of a suture is positioned between the second cam surface 272 and the second suture backstop 274 and the second locking lever 270 may be moved into a locked position for securing the second end of the suture to the second suture clamping assembly, with the suture thread being squeezed between the second cam surface 272 and the second suture backstop 274. In another embodiment, the end of the suture may be tied in a loop or knot around a post (shown, not labeled) and aligned by way of an alignment notch or the backstop 274. In one embodiment, the second suture mount 268 is preferably secured to a concave side of the second large gear 266, whereupon the second large gear 266 and the second suture mount 268 are adapted to rotate simultaneously with one another between the zero degree position and the 90 degree position, which, in turn, rotates the suture on its axis between the zero degree position and the 90 degree position. In one embodiment, the second suture mount 268 preferably allows for translation about the axis of rotation to enable the suture to stretch while still applying the same amount of tension and maintaining the alignment with the second large gear 266.

In one embodiment, the upper end of the tensioning cable 182 is secured to the linear slide 165 (FIGS. 13-15), which, in turn, is connected with the second suture mount 268. The tensioning cable 182 desirably passes over the pulley 192 whereupon a lower end of the tensioning cable 182 is secured to the tensioning weight 186 and an upper end of the tensioning cable is secured to the linear slide 165 for tensioning the second end of the suture that is secured to the second suture mount 268 of the second suture clamping assembly 164.

Figure 16:
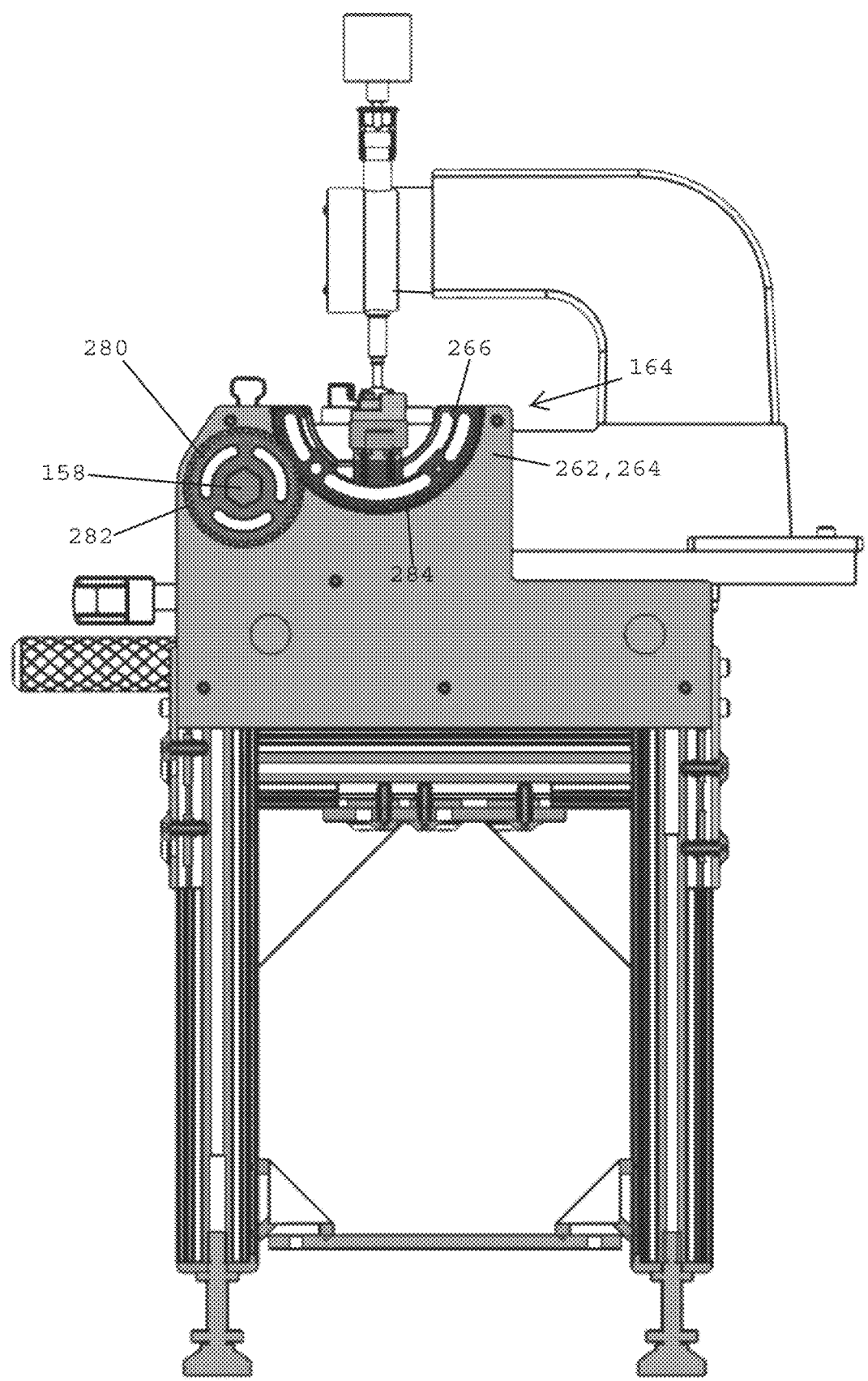
FIG. 16 is a cross-sectional view of the right side of the system shown in FIG. 1 including a second small gear and a second large gear of the second suture clamping assembly of FIG. 15, in accordance with one embodiment of the present patent application.
Figure 17:
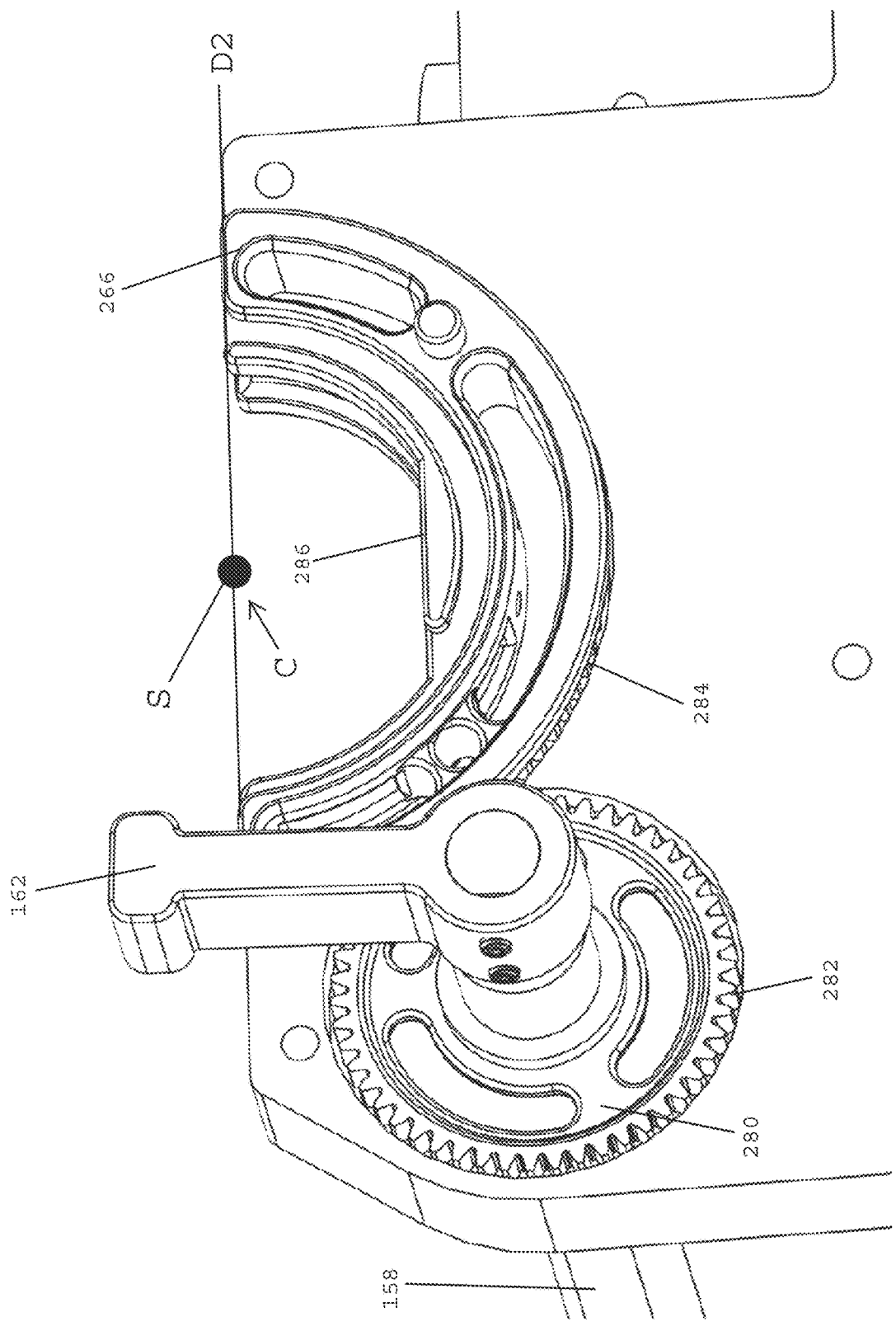
FIG. 17 is an exploded view of the second small gear and the second large gear shown in FIG. 16.

Referring to FIGS. 16 and 17, in one embodiment, the second large gear 266 is held between the second outer and inner gear plates 262, 264 (FIG. 15) of the second suture clamping assembly 164.

In one embodiment, the second large gear 266 preferably has the shape of a half circle. In one embodiment, the second large gear 266 desirably has a convexly curved outer surface having gear teeth 284 that are adapted to mesh with the gear teeth 282 of the second small gear 280. The second large gear 266 preferably has a concave curved inner surface with a centrally located mounting platform 286 that is adapted to seat the second suture mount 268 (FIG. 15). Similar to the first large gear 214 shown and described above in FIGS. 10A and 10B, in one embodiment, the lateral sides of the second large gear 266 have respective curved guide flanges that define respective curved grooves that are adapted to receive curved retaining lips on the second outer and inner gear plates 262, 264 (FIG. 15) for enabling the second large gear to rotate relative to the gear plates.

Referring to FIG. 17, in one embodiment, the second large gear 266 is a half circle and has a diameter D2 that intersects with the center C of the circle. In one embodiment, when a second end of the suture S is secured to the second suture clamping assembly 164 (FIG. 1), the suture S is preferably aligned with the center C and is held in the center C as the second large gear 266 rotates between the first zero degree position and the second 90 degree position. In one embodiment, the first and second suture clamping assemblies 150, 164 (FIG. 1) preferably hold the suture S taut so that it remains aligned within the center C as the suture S is rotated on its axis from the first zero degree position to the second 90 degree position.

In one embodiment, rotation of the rotatable bar 158 will rotate the second small gear 280, which, in turn, will rotate the second large gear 266 between the zero degree position and the 90 degree position. As the second large gear 266 rotates, the second suture mount 268 (FIG. 15) rotates simultaneously with the second large gear, which, in turn, will rotate the suture S that is secured to the second suture clamping assembly 164.

Referring to FIG. 17, in one embodiment a right lever 162 is preferably coupled with the right end of the rotatable bar 158. In one embodiment, rotating the right lever 162 from the vertical orientation shown in FIG. 17 to a horizontal orientation will rotate the rotatable bar 158 in a counter-clockwise direction, which, in turn, will rotate the second small gear 280 in a counterclockwise direction. As the second small gear 280 rotates in the counterclockwise direction, the gear teeth 282 of the second small gear preferably engage the gear teeth 284 of the second large gear 266 for rotating the second large gear 266 in a clockwise direction between the zero degree position and the 90 degree position. Although not shown in FIG. 17, the second suture mount 268 (FIG. 15) that is secured to a central platform 286 of the second large gear 266 will rotate simultaneously with the second large gear 266.

Figure 18:
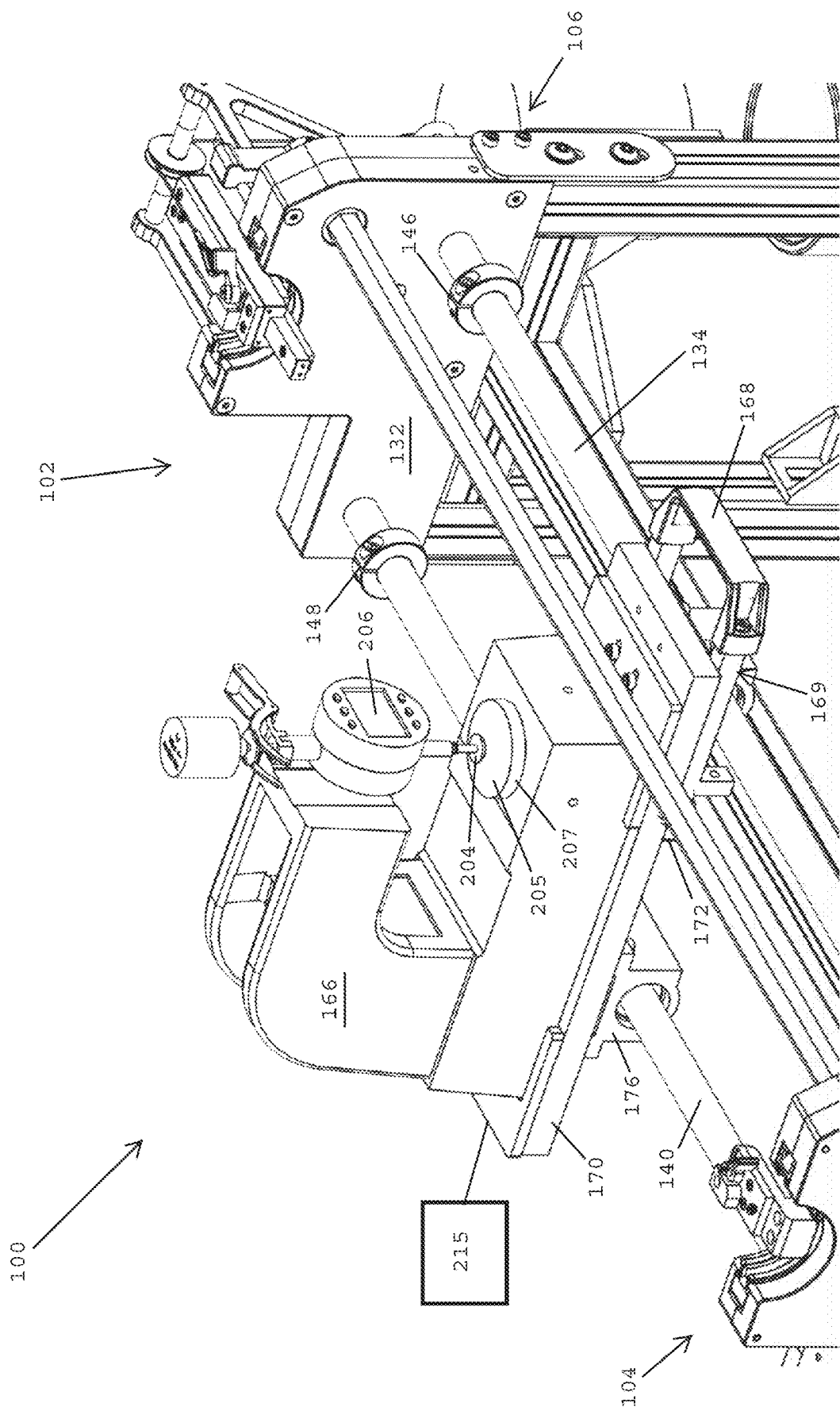
FIG. 18 shows a perspective view of the system of FIG. 1 including a suture diameter measurement gauge, in accordance with one embodiment of the present patent application.

Referring to FIG. 18, in one embodiment, the system 100 for measuring the diameter of a suture preferably includes the suture diameter gauge 166, which is adapted to slide along the respective front and rear guide rails 134, 140 for being positioned at selected points and/or locations between the left and right sides 104, 106 of the test bench 102. In one embodiment, the suture diameter gauge 166 preferably includes a gauge base plate 170 having a front bearing 172 that is secured to an underside of the gauge base plate 170 and a rear bearing 176 that is also secured to the underside gauge base plate 170. The front and rear bearings 172, 176 desirably have openings that are adapted to receive the outer surfaces of the respective front and rear guide rails 134, 140 for enabling the suture diameter gauge 166 to slide between the left and right ends of the test bench 102. In one embodiment, the test bench 102 desirably includes a front guide rail stop 146 that is secured over the front guide rail 134 and a rear guide rail stop 148 that is secured over the rear guide rail 140. The stops 146, 148 may be located adjacent the right ends of the front and rear guide rails. As an operator slides the suture diameter gauge 166 toward the right side 106 of the test bench 102, the front and rear guide rail stops 146, 148 may contact the respective front and rear bearings 172, 174 or a side of the suture diameter gauge 166 for halting the sliding movement of the suture diameter gauge toward the right end plate assembly 132 so that the side of the suture diameter gauge 166 does not engage, contact, and/or strike the right end plate assembly 132 of the test bench 102.

In one embodiment, the suture diameter gauge 166 preferably includes a brake assembly 169 that is coupled with the suture diameter gauge handle 168. When deployed, the brake assembly 169 prevents the suture diameter gauge 166 from sliding over the front and rear guide rails. In one embodiment, the brake assembly 169 may be moved into a first position in which the suture diameter gauge is free to slide over the front and rear guide rails 134, 140, and a second position (i.e., the braking position) in which the suture diameter gauge is locked in place on the front and rear guide rails 134, 140. In one embodiment, the brake assembly 169 may include a spring-loaded sliding joint, whereby when the suture diameter gauge handle 168 is pressed the brake assembly 169 is released and when the suture diameter gauge handle is released the brake is applied to halt sliding movement of the suture diameter gauge.

Figure 19:
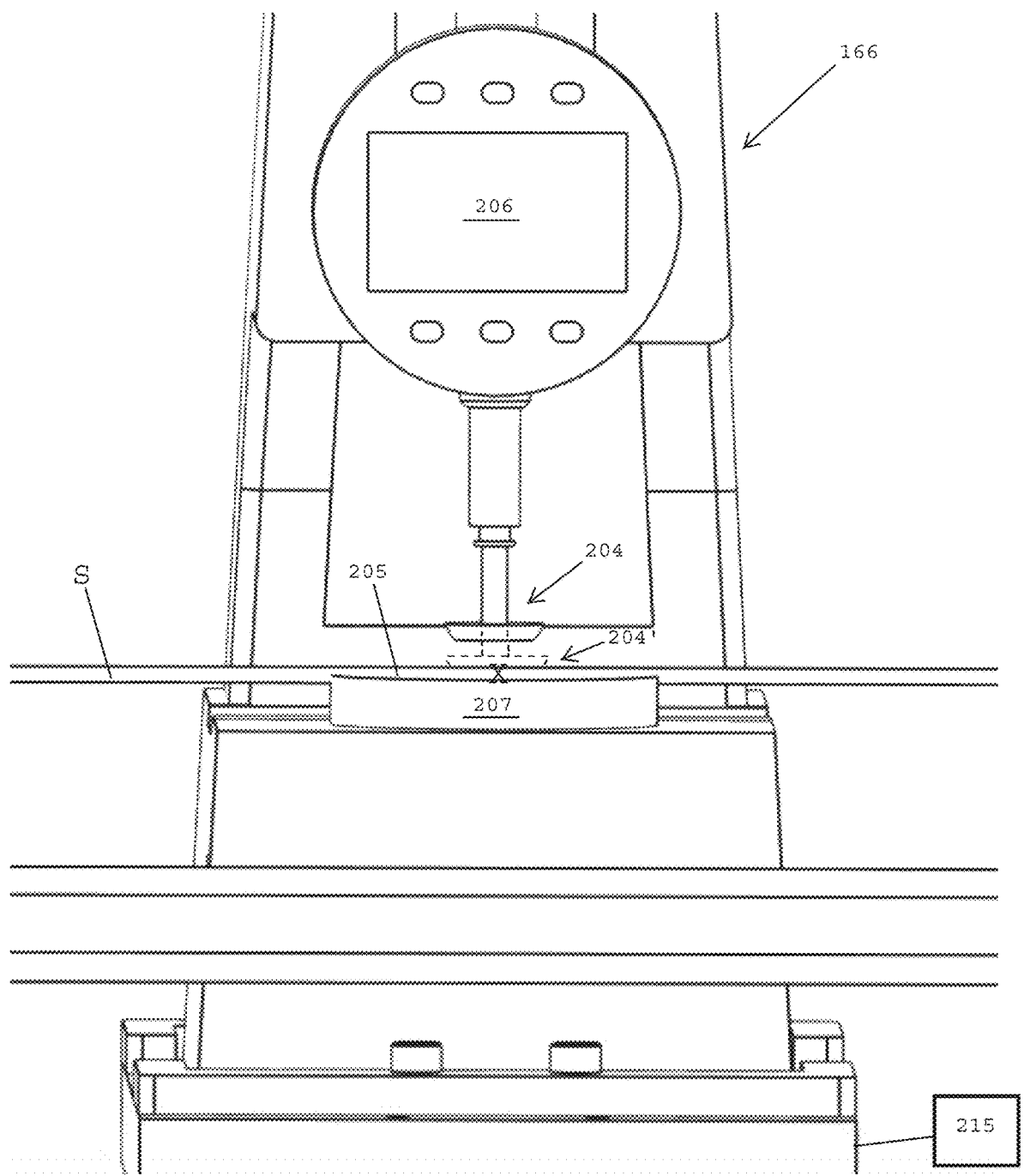
FIG. 19 shows a front elevation view of the suture diameter measurement gauge of FIG. 18.

Referring to FIGS. 18 and 19, in one embodiment, the suture diameter gauge 166 preferably includes a test probe 204 that may be lowered toward a top surface 205 of a measuring platform 207 for measuring the diameter of a suture S (FIG. 19) that has been positioned between the lower end of the test probe 204 and the flat top surface 205 of the measuring platform 207. In one embodiment, the system preferably includes an actuator 215, such as a depressible foot pedal, which is coupled with the suture diameter gauge and that may be engaged by an operator for lowering the test probe 204 onto the suture to measure the diameter of the suture S at the location designated X.

In FIG. 19, reference number 204 shows the test probe in a retracted position in which the test probe is spaced away from the flat top surface 205 of the measuring platform 207 and is not in contact with the suture S. When the test probe is in the retracted position, the brake assembly of the suture diameter gauge 166 may be engaged for sliding the gauge to the left or the right relative to the suture S for locating the gauge at a different location along the length of the suture S. In FIG. 19, reference number 204' and the dashed lines represent the test probe in an extended position in which the lower end of the test probe 204' engages the suture S for obtaining a diameter reading for the suture at the location designated X.

In one embodiment, the system preferably includes a controller (e.g., electronics, microprocessors, software programs, sensors, memory devices, etc.) for lowering the test probe toward the measuring platform 207 and the suture S in a controlled manner so that the test probe is not simply dropped onto the suture S (e.g., as a dead weight), which could distort and/or deform the shape of the suture S, resulting in the collection of inaccurate diameter readings for the suture S. The control system may be configured to lower the test probe at a controlled rate of descent and with a controlled level of force (e.g., total dead load) in a manner that is standardized, consistent, and repeatable for obtaining reliable and repeatable diameter measurement readings. Automating and standardizing the probe lowering protocol provides a dramatic improvement over prior art methodologies in which operators control the movement of the test probe manually and/or by hand, which may result in great variances between cycles and between operators. Automating the system disclosed herein removes operator error and eliminates variances between different operators.

In one embodiment, the suture diameter gauge and the integrated control system may lower the test probe using pneumatic and mechanical components including but not limited to pistons, plungers, springs, snubbers and air gaps. The test probe may also be lowered electronically or by using optical systems. In one embodiment, the test probe may be returned to the retracted position electronically or by using electronic components.

In one embodiment, the test probe is normally in a lowered or extended position in which the test probe is resting atop the testing platform. In one embodiment, when the actuator 215 is in a first position (e.g., a foot pedal is depressed), the lower end of the test probe 204 is retracted so that the test probe is not in contact with the suture S. In one embodiment, when the actuator 215 is moved into a second position (e.g., the foot pedal is released), the system sends a signal (e.g., an electronic signal) to the suture diameter gauge 166 to slowly lower the test probe 204 until the lower end of the test probe contacts the suture S for obtaining a diameter measurement for the suture. In one embodiment, the lowering of the test probe may be dampened such as by coupling a piston or pneumatic device with the test probe. In one embodiment, the system is programmed to lower the test probe at a controlled rate of descent so that the test prove does not permanently deform and/or bounce on the top of the suture.

In one embodiment, the suture diameter gauge is configured and/or programmed to control the total dead load that is applied to a suture so that the same, consistent dead load is applied each time the test probe is lowered. In one embodiment, industry standards (e.g., USP 861) may be used for determining the total dead load that is to be applied to the suture. In one embodiment, the gauge preferably applies a greater total dead load for larger sutures and a smaller total dead load for smaller sutures. For example, the gauge may be configured to apply a total dead load of about 210 grams to sutures that are size 7-0 or larger, and a total dead load of not greater than about 60 grams for sutures having a size of 8-0 or smaller. In other embodiments, the total dead load applied by the suture diameter gauge may be recalibrated and/or re-programmed to comply with other standards such as those required by European or non-U.S jurisdictions.

In one embodiment, the suture diameter gauge 166 desirably includes a digital display 206 that displays the results of the most recent diameter measurement for the suture S that is positioned over the top surface 205 of the measuring platform 207. In one embodiment, after a first diameter measurement is obtained, the suture is rotated by 90 degrees and a second diameter measurement is recorded, whereby the first and second diameter measurements are recorded at the same point along the length of the suture with the first measurement taken at a right angle to the second measurement. As a result, a first diameter measurement of the suture S may be obtained for the suture S at the zero degree position, and, while maintaining the suture diameter gauge at the same point along the length of the suture S, rotating the suture S to the 90 degree position so that a second diameter measurement of the suture S may be obtained for the suture S at the 90 degree position.

Figure 20:
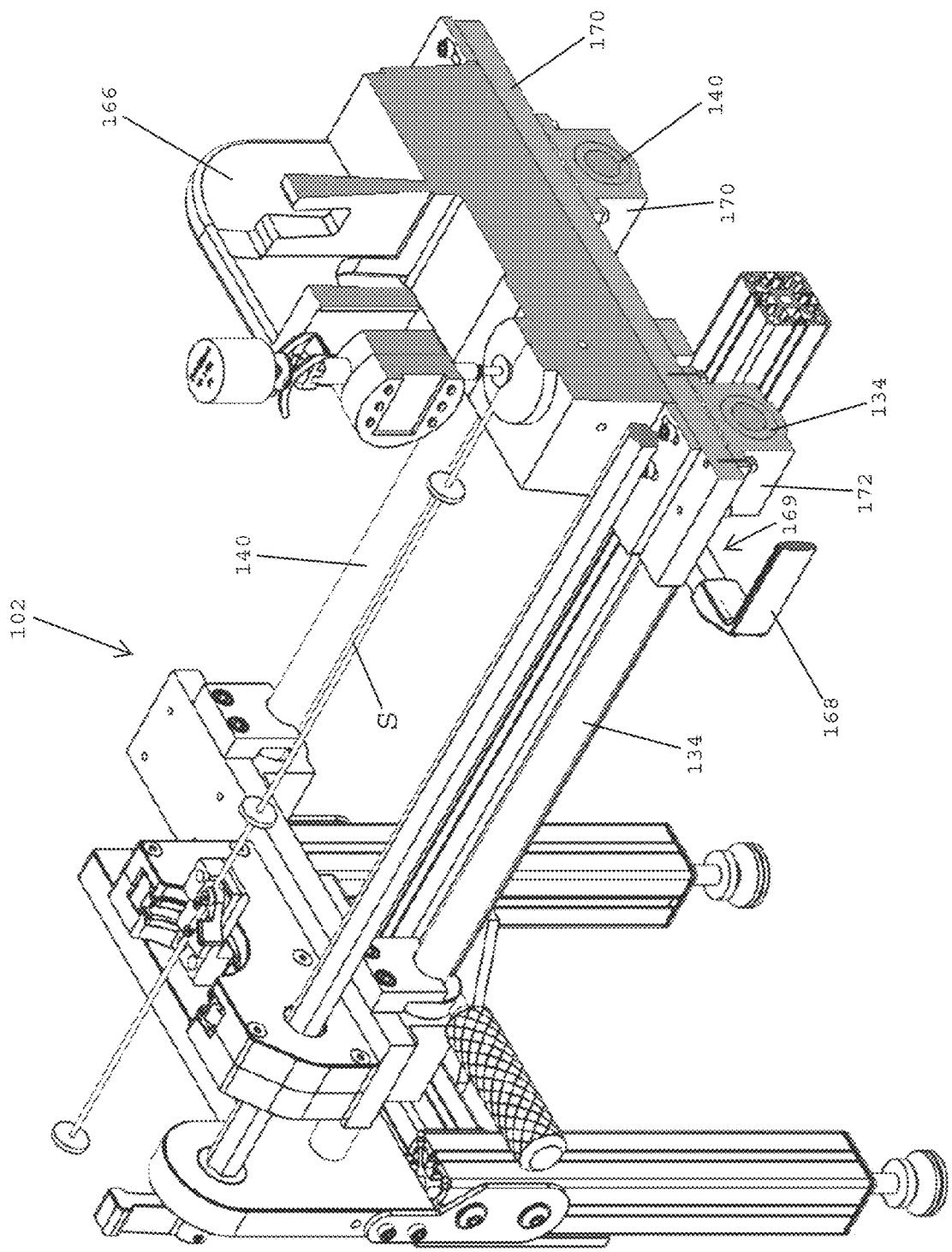
FIG. 20 shows a perspective, cross-sectional view of the suture diameter measurement gauge shown in FIGS. 18 and 19.
Figure 21:
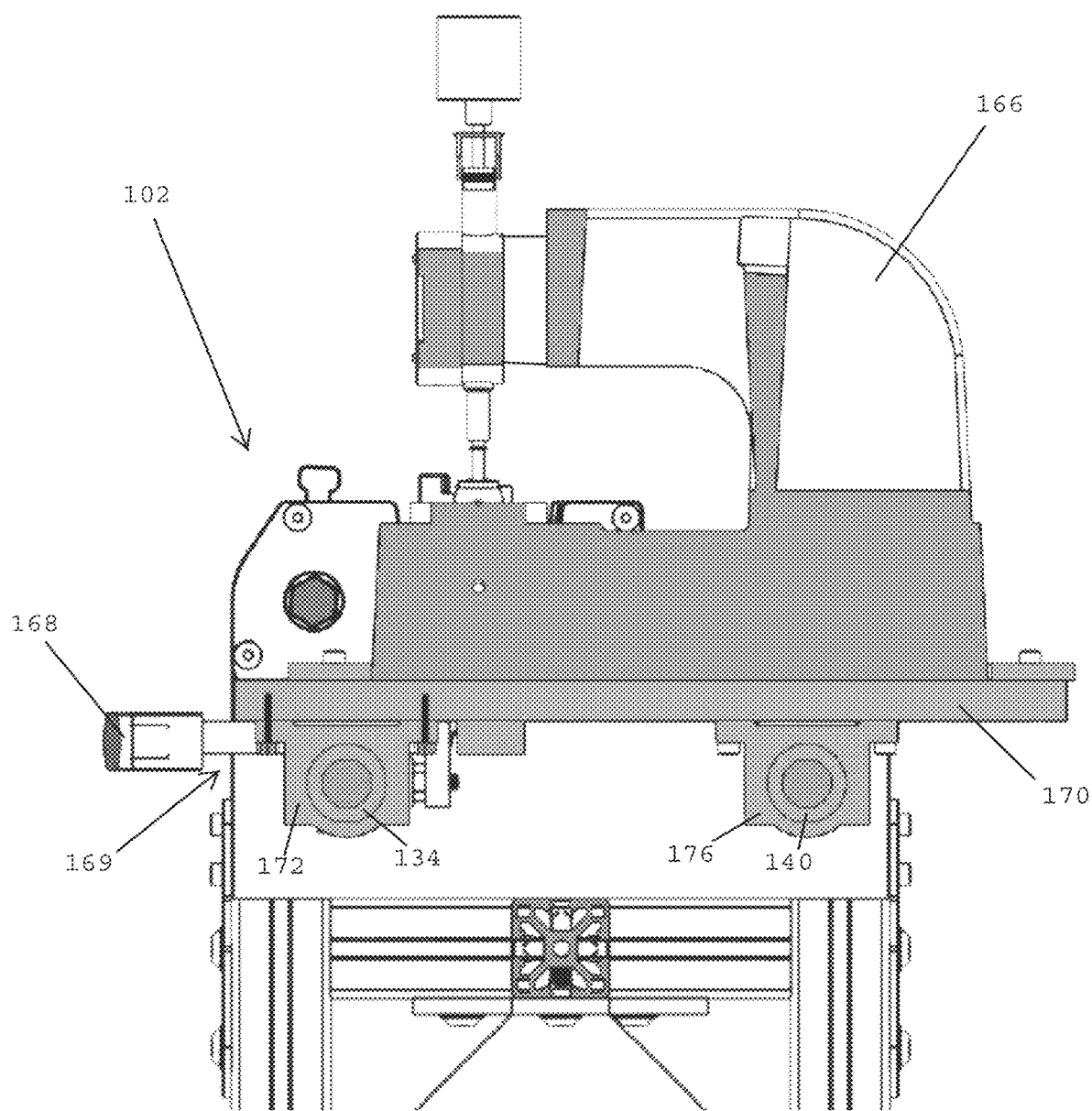
FIG. 21 shows another cross-sectional view of the suture diameter measurement gauge shown in FIGS. 18-20.

Referring to FIGS. 20-22, in one embodiment, the suture diameter gauge 166 is desirably mounted on the front and rear guide rails 134, 140 of the test bench 102 for enabling the suture diameter gauge to slide between the left and right sides of the test bench for measuring the diameter of a suture at various locations along the length of the suture. In one embodiment, the suture diameter gauge 166 preferably includes the gauge base plate 170 and the front and rear bearings 172, 176 secured to an underside of the gauge base plate 170. Each of the bearings 172, 176 preferably has an opening extending therethrough that is adapted to receive one of the respective front and rear guide rails 134, 140 for coupling the suture diameter gauge with the guide rails, whereby the suture diameter gauge may slide over the guide rails.

In one embodiment, the suture diameter gauge 166 preferably includes the brake assembly 169 that is coupled with the suture diameter gauge handle 168. When deployed, the brake assembly 169 prevents the suture diameter gauge 166 from sliding over the front and rear guide rails 134, 140. In one embodiment, the brake assembly 169 may be moved into a first position in which the suture diameter gauge is free to slide over the front and rear guide rails 134, 140, and a second position (i.e., the braking position) in which the suture diameter gauge is locked in place on the front and rear guide rails 134, 140. In one embodiment, the brake assembly 169 may include a spring-loaded sliding joint 171 (FIG. 22), whereby when the suture diameter gauge handle 168 is pressed the brake assembly 169 is released and when the suture diameter gauge handle 168 is released the brake assembly 169 is applied to halt sliding movement of the suture diameter gauge.

Referring to FIG. 22, in one embodiment, the front bearing 172 preferably has a front opening 174 extending therethrough that is adapted to receive the front guide rail 134. In one embodiment, the rear bearing 176 desirably includes a rear opening 178 extending therethrough that is adapted to receive the rear guide rail 140. The front and rear bearings 172, 176 are desirably mounted to an underside of the gauge base plate 170 for enabling the suture diameter gauge 166 to slide along the respective lengths of the front and rear guide rails 134, 140 for moving the suture diameter gauge to selected points and/or locations between the left and right sides 104, 106 (FIG. 1) of the test bench 102.

In one embodiment, the suture diameter gauge 166 preferably includes a suture diameter gauge handle 168 that may be grasped by an operator at the front side 200 of the test bench 102 for enabling an operator to selectively move the suture diameter gauge 166 between the left and right ends of the test bench 102. The gauge handle 168 may include the brake assembly coupled therewith that locks the suture diameter gauge in place at selected locations along the lengths of the respective front and rear guide rails 134, 140. In one embodiment, the suture diameter gauge 166 will remain locked in place on the guide rails until the gauge handle 168 is re-engaged for unlocking the suture diameter gauge to allow for sliding movement over the front and rear guide rails.

Figure 23A:
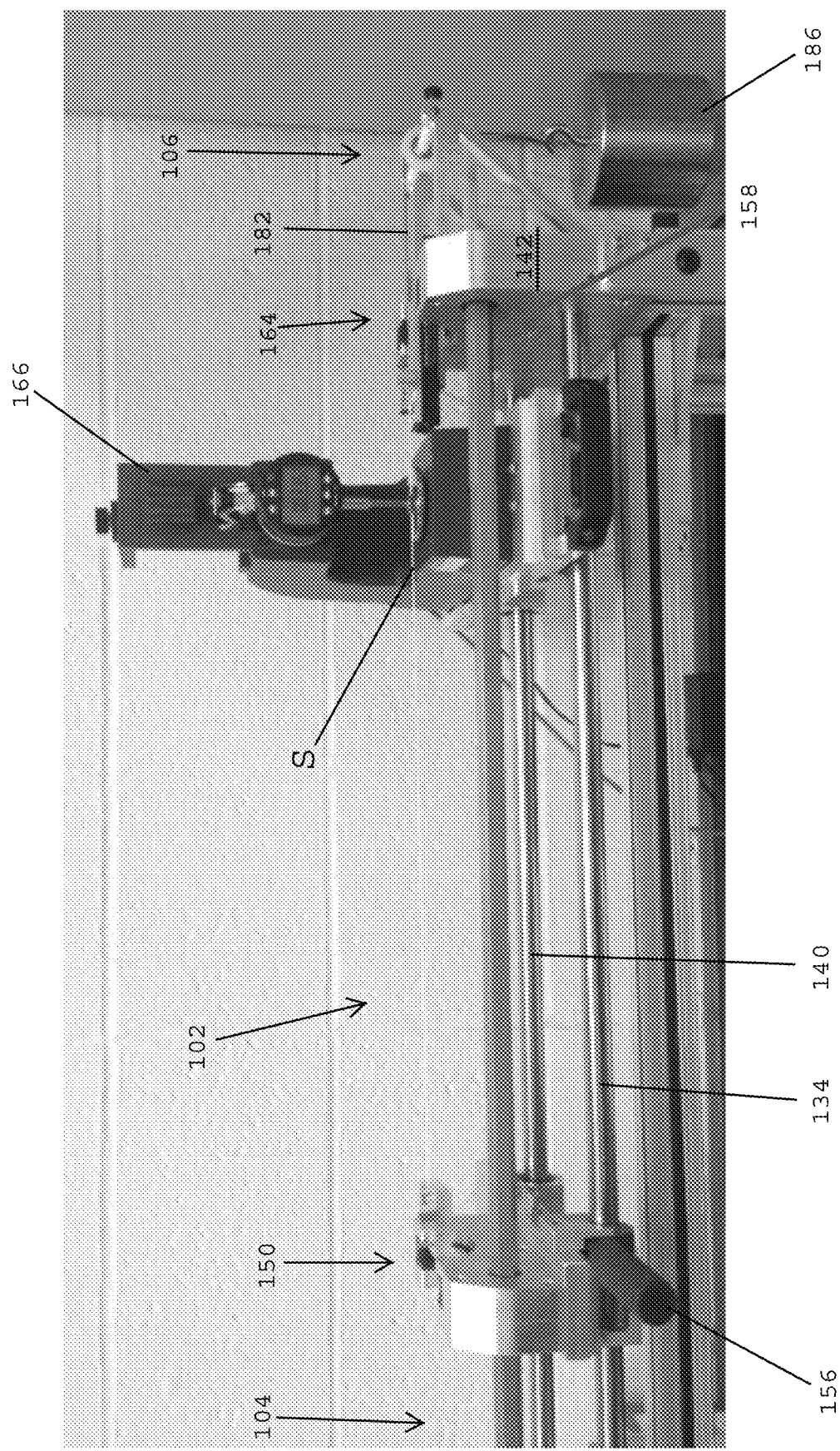
FIG. 23A shows a front view of a system for measuring the diameters of sutures including first and second suture clamping assemblies in a zero (0) degree position, in accordance with one embodiment of the present patent application.

Referring to FIG. 23A, in one embodiment, a surgical suture S may be secured to the first and second suture clamping assemblies 150, 164 of the test bench 102 for measuring the diameter of a surgical suture S. In one embodiment, a first end of the suture S is secured to the first suture clamping assembly 150 located at the left side 104 of the test bench 102. The first suture clamping assembly 150 preferably includes the locking handle 156 that may be moved to an unlocked position for enabling the first suture clamping assembly 150 to slide left and right along the front and rear guide rails 134, 140 for changing the distance between the first and second suture clamping assemblies 150, 164. In one embodiment, with the locking handle 156 in the unlocked position, the first suture clamping assembly 150 may be slid over the front and rear guide rails for adjusting the distance between the first suture clamping assembly 150 and the second suture clamping assembly 164. In one embodiment, the first and second suture clamping assemblies 150, 164 may be positioned further away from one another for measuring a suture having a greater length, and the first and second suture clamping assemblies 150, 164 may be positioned closer together for measuring a suture having a shorter length. When the first suture clamping assembly 150 has been positioned at a selected location that is a preferred distance from the second suture clamping assembly 164, the locking handle 156 may be moved to a locked position for locking the first suture clamping assembly 150 in place along the length of the front and rear guide rails 134, 140. With the locking handle 156 in the locked position, the distance between the first and second suture clamping assemblies will remain constant.

In one embodiment, the second end of the surgical suture S is preferably secured to the second suture clamping assembly 164. As noted herein, in one embodiment, the second suture clamping assembly 164 is preferably stationary and does not slide left or right along the length of the front and rear guide rails 134, 140. In one embodiment, the tensioning weight 186 preferably tensions the tension cable 182 for applying tension to the second suture mount 268, which, in turn, applies tension to the second end of the surgical suture S that has been secured to the second suture clamping assembly 164. With tension applied to the suture S, the suture S is preferably held taut (i.e., pulled tight under tension) between the first and second suture clamping assemblies 150, 164.

In one embodiment, the suture diameter gauge 166 may be utilized for measuring the diameter of the surgical suture S. The suture diameter gauge 166 is preferably adapted to slide between the first suture clamping assembly 150 and the second suture clamping assembly 164 and along the lengths of the respective front and rear guide rails 134, 140 so that the suture diameter gauge may measure the diameter of the suture S at different points along the length of the suture S. The brake assembly coupled with the suture diameter gauge handle may be used for locking the suture diameter gauge at a selected location along the length of the front and rear guide rails. In one embodiment, with the suture diameter gauge 166 at a first point between the left and right sides 104, 106 of the test bench 102, a first diameter measurement is obtained for the surgical suture S. After obtaining the first diameter measurement, the first and second suture clamping assemblies 150, 164 are rotated 90 degrees from a zero degree position to a 90 degree position, which, in turn, rotates the suture S by 90 degrees. After obtaining a first diameter reading at zero degrees and a second diameter reading at 90 degrees, the handle may be engaged for unlocking the brake assembly so that the suture diameter gauge 166 may be slid to a second point along the length of the suture S. Once the suture diameter gauge is located at the second point, the handle may be released for deploying the brake assembly to lock the suture diameter gauge in place at the second point, whereupon a second set of diameter measurements may be obtained, e.g., a first diameter measurement taken at the zero degree position and a second diameter measurement taken at the 90 degree position. The process may be repeated (e.g., unlocking and locking the brake assembly), so that diameter measurements may be obtained at 3-5 different locations along the length of the suture S, with each set of measurements including a first diameter measurement at the zero degree position and a second diameter measurement at the 90 degree position.

Figure 23B:
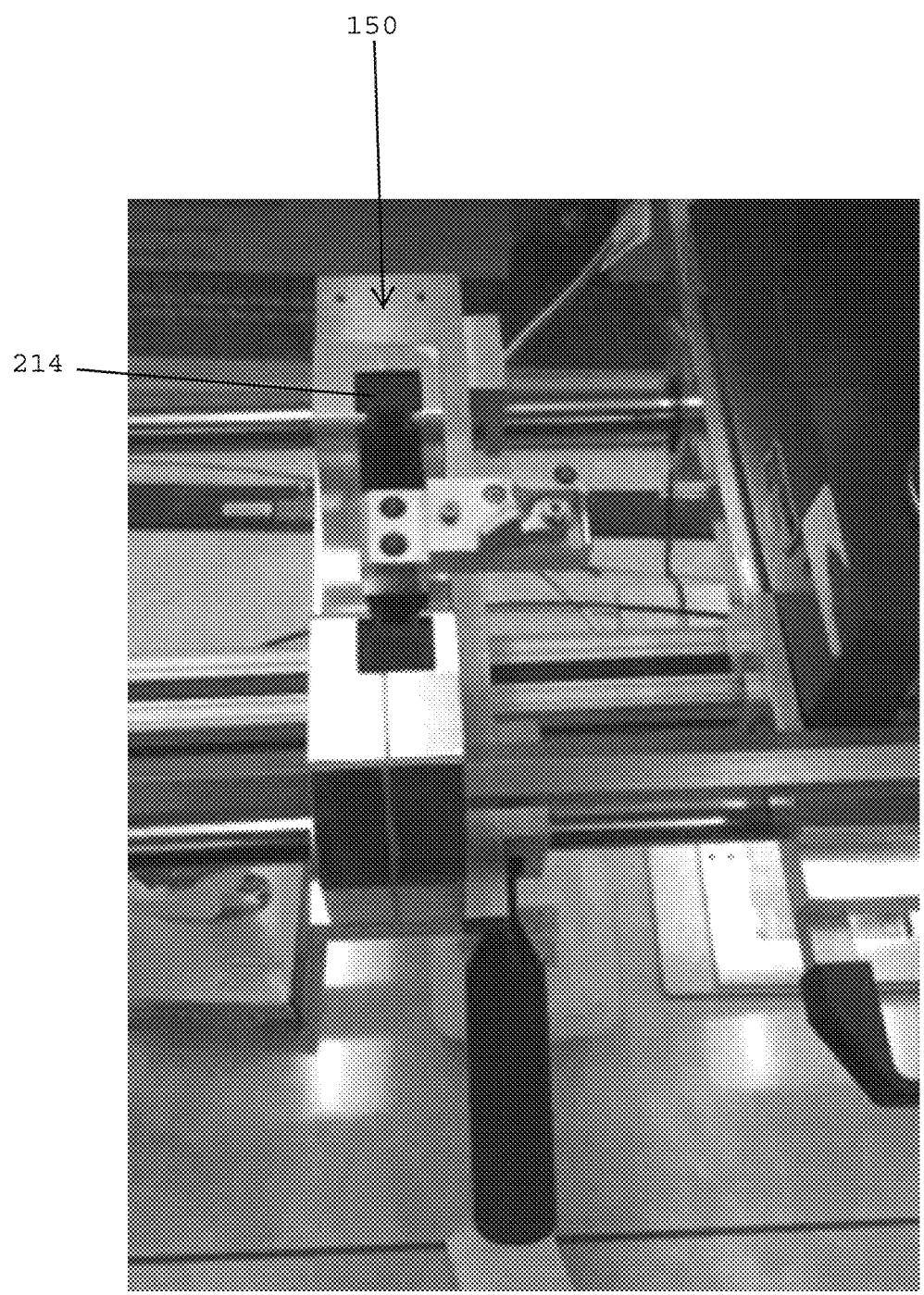
FIG. 23B shows a perspective view of the first suture clamping assembly of FIG. 23A.
Figure 23C:
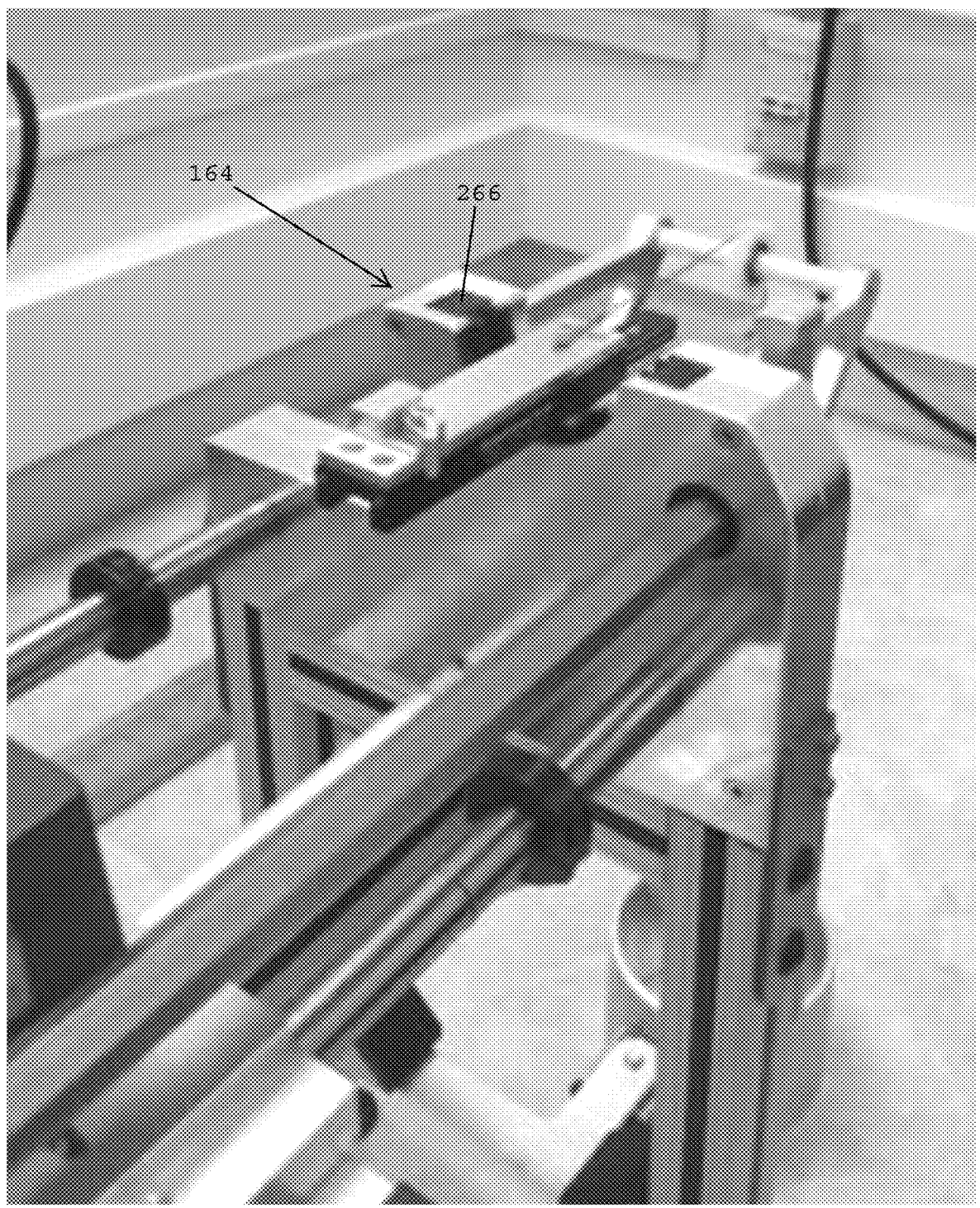
FIG. 23C shows a perspective view of the second suture clamping assembly of FIG. 23A.

Referring to FIGS. 23A-23C, in one embodiment, the first and second large gears 214, 266 of the respective first and second suture clamping assemblies 150, 164 are desirably positioned at the zero degree position. In the zero degree position, the suture diameter gauge 166 is utilized for obtaining a diameter measurement for the suture S.

Figure 24A:
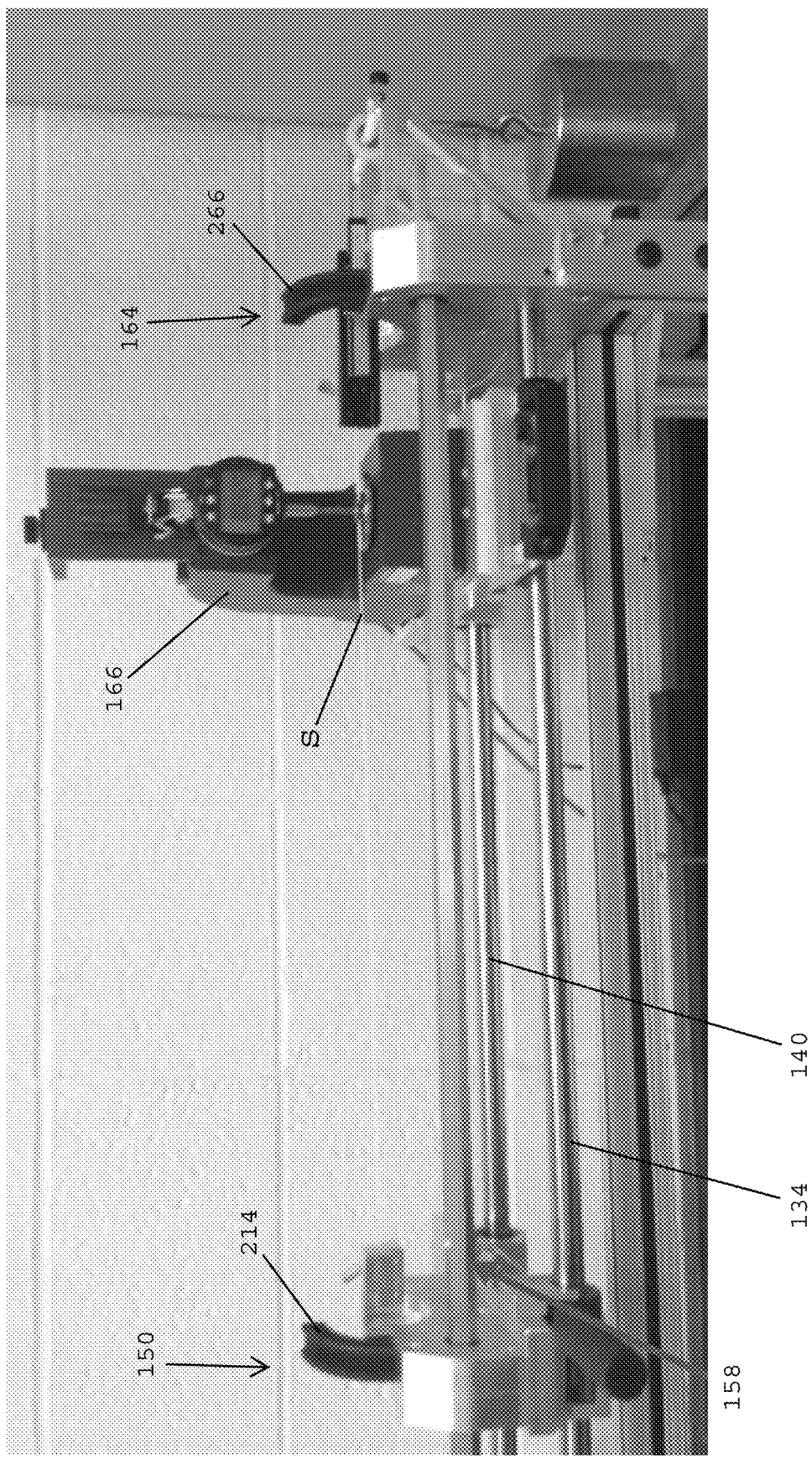
FIG. 24A shows the system of FIG. 23A with the first and second suture clamping assemblies rotated into a 90 degree position, in accordance with one embodiment of the present patent application.
Figure 24B:
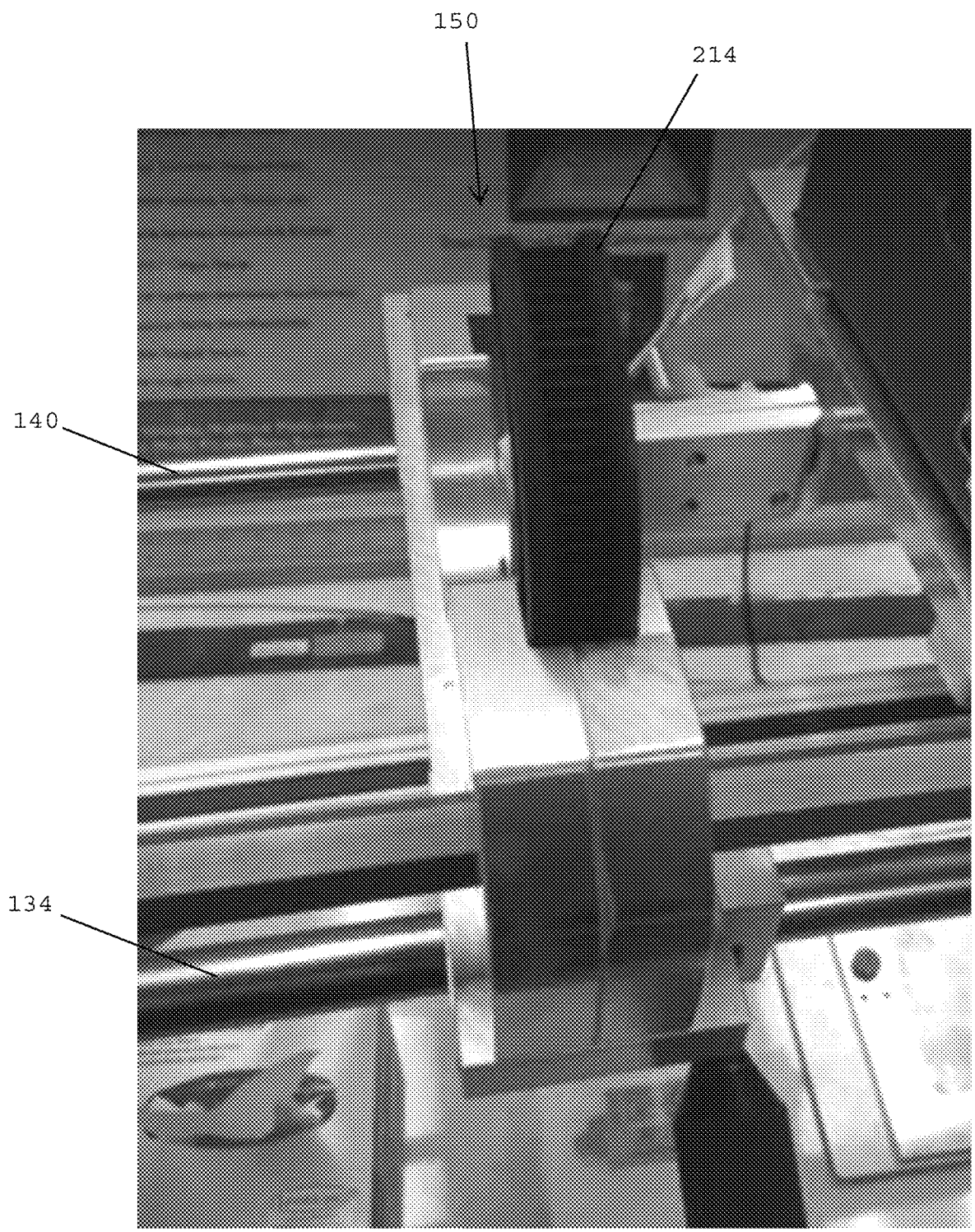
FIG. 24B shows a front perspective view of the first suture clamping assembly of FIG. 24A.
Figure 24C:
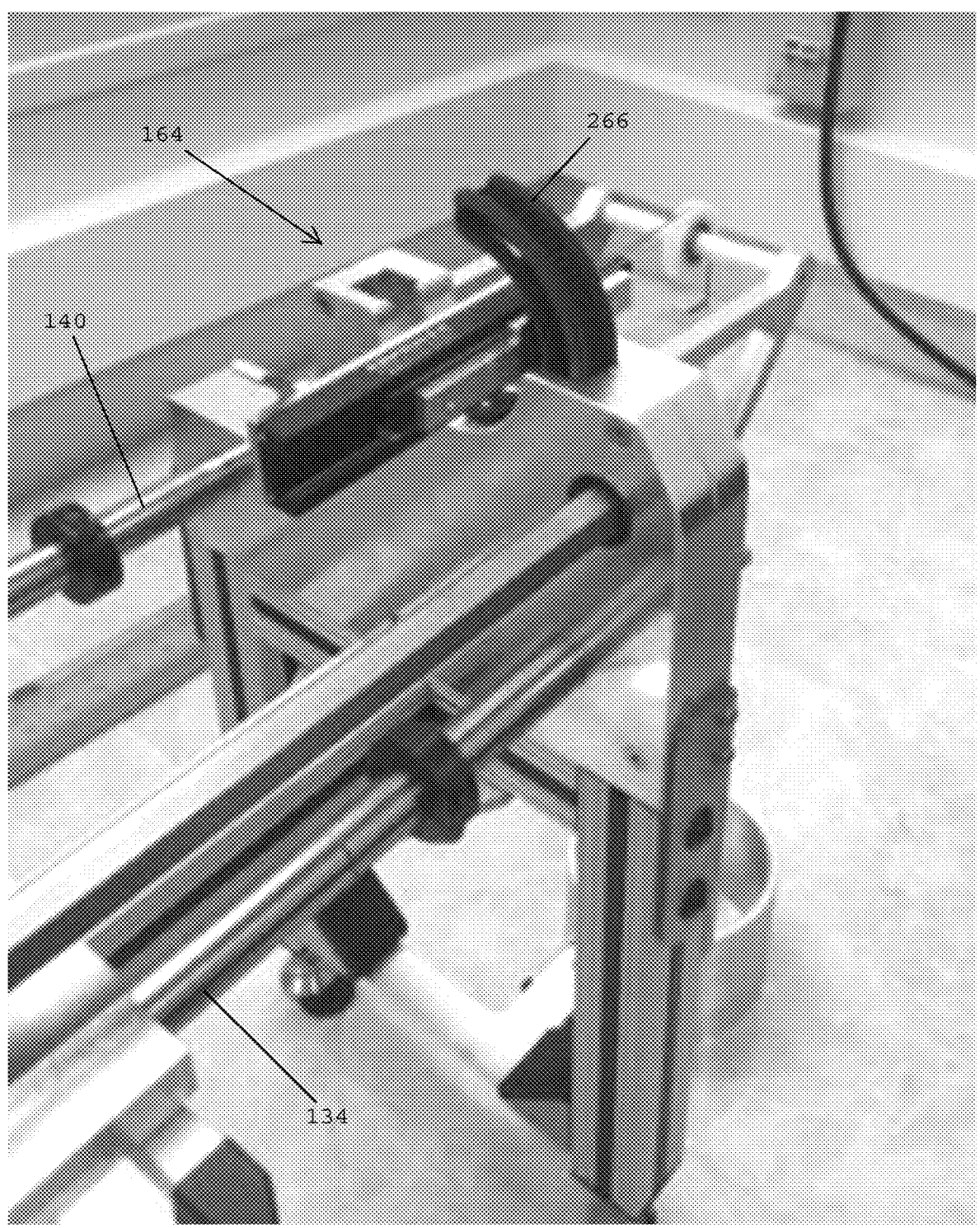
FIG. 24C shows a perspective view of the second suture clamping assembly of FIG. 24A.

Referring to FIGS. 24A-24C, after the diameter of the suture has been measured with the suture at the zero degree position, without moving the suture diameter gauge 166, the first and second large gears 214, 266 of the first and second suture clamping assemblies 150, 164 may be rotated by 90 degrees to the 90 degree position, which, in turn, simultaneously rotates the suture S by 90 degrees. The suture diameter gauge 166 will preferably be activated to obtain another diameter measurement of the suture S at the same point along the length of the suture S.

In one embodiment, after obtaining the first set of diameter measurements, the suture diameter gauge 166 may be slid to the left along the front and rear guide rails 134, 140, to a second point along the length of the suture S, for obtaining a second set of diameter measurements for the suture S at the zero degree position and the 90 degree position. The process may be repeated so that multiple sets of diameter measurements may be obtained, with each set including a first diameter measurement at the zero degree position and a second diameter measurement at the 90 degree position.

Referring the FIG. 25, in one embodiment, the distance between the first suture clamping assembly 150 and the second suture clamping assembly 164 may be modified to accommodate sutures having different lengths. In one embodiment, the second suture clamping assembly 164 is fixed to the test bench so that it remains stationary and the first suture clamping assembly 150 is configured to slide and move relative to the second suture clamping assembly 164. In one embodiment, sutures having lengths between 4-48 inches may be secured to the suture clamping assemblies, whereby the first suture clamping assembly is moved to accommodate the different suture lengths. In one embodiment, the system may accommodate shorter sutures (e.g., sutures having lengths of one to six inches) or longer sutures (e.g., sutures having lengths of four to 10 feet or greater).

Referring to FIG. 25, in one embodiment, the suture S has a length of about 45-55 inches and the first and second suture clamping assemblies 150, 164 are spaced away from one another by a distance $D_1$ of about 45-55 inches so that the suture S is stretched taut between the first and second suture clamping assemblies 150, 164.

Referring to FIG. 26, in one embodiment, the suture S' has a length of about 20-30 inches and the first and second suture clamping assemblies 150', 164' are spaced away from one another by a distance $D_2$ of about 20-30 inches so that the suture S' is stretched taut between the first and second suture clamping assemblies.

Referring to FIG. 27, in one embodiment, the suture S" has a length of about 4-10 inches and the first and second suture clamping assemblies 150", 164" are spaced away from one another by a distance $D_3$ of about 4-10 inches so that the suture S" is stretched taut between the first and second suture clamping assemblies.

Figure 28A:
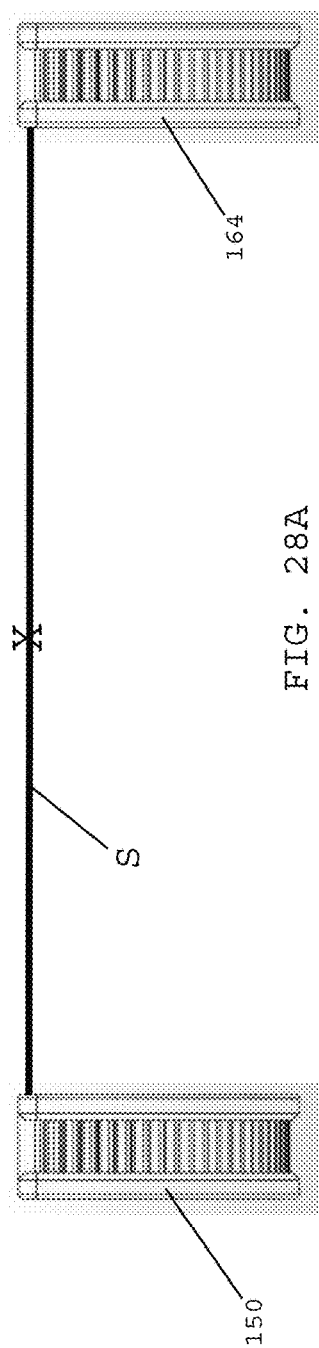
FIG. 28A is a schematic view of a suture having a first end secured to a first suture clamping assembly and a second end secured to a second suture clamping assembly, wherein the first and second suture clamping assemblies and the suture are in a zero degree position, in accordance with one embodiment of the present invention.
Figure 28B:
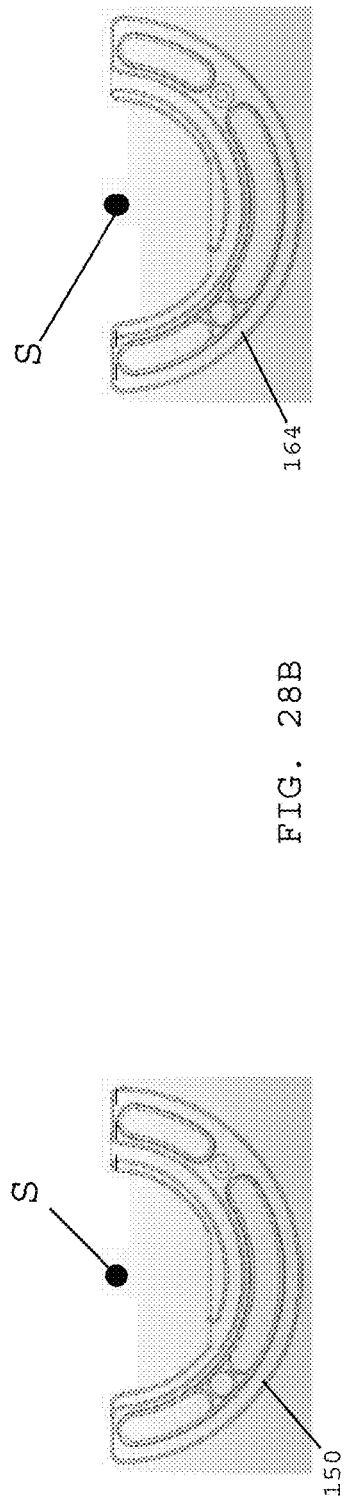
FIG. 28B is a schematic view of the first and second suture clamping assemblies of FIG. 28A.
Figure 29:
FIG. 29 is a schematic view of the first and second suture clamping assemblies of FIGS. 28A and 28B after the first and second suture clamping assemblies have been rotated by 90 degrees to the 90 degree position.

Referring to FIGS. 28A-28B and 29, in one embodiment, the first and second suture clamping assemblies 150, 164 preferably apply tension to the suture S so that the suture S is stretched taut (e.g., held under tension) as the first and second suture clamping assemblies rotate between the zero degree position and the 90 degree position.

Referring to FIGS. 28A and 28B, in one embodiment, with the first and second suture clamping assemblies 150, 164 in the zero degree position, the first end of the suture S is secured to the first suture clamping assembly 150 and the second end of the suture S is secured to the second suture clamping assembly 164. In one embodiment, tension is applied to the suture S through the linear slide 165 (FIG. 3) connected with the second suture clamping assembly 164 so that the suture S is held taut (i.e., stretched tight with no slack) between the first and second suture clamping assemblies. In one embodiment, the suture diameter gauge 166 (FIG. 23A) is utilized for measuring the diameter of the suture S at a designated point X (FIG. 28A) along the length of the suture.

Referring to FIGS. 28B and 29, the first and second suture clamping assemblies 150, 164 are simultaneously rotated from the zero degree position shown in FIG. 28B to the 90 degree position shown in FIG. 29. As the first and second suture clamping assemblies 150, 164 are simultaneously rotated by 90 degrees, the suture S that is held taut by the first and second suture clamping assemblies is also rotated on its axis by 90 degrees. After the suture S has been rotated by 90 degrees, the suture diameter gauge 166 (FIG. 23A) may be utilized for measuring the diameter of the rotated suture S at the designated point X (FIG. 28A) along the length of the suture. Thus, two diameter readings are obtained for the suture S at the same designated point X along the length of the suture, with the first and second diameter readings being taken 90 degrees apart from one another (e.g., at right angles relative to one another).

Figure 30A:
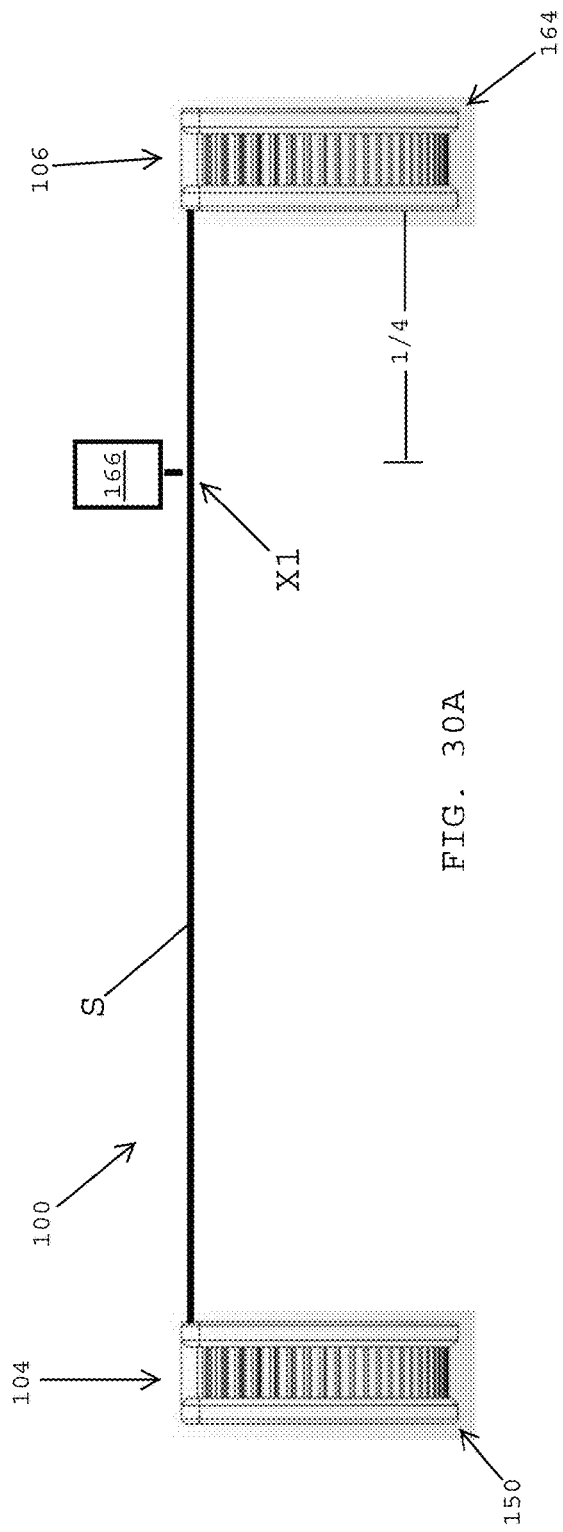
FIG. 30A is a schematic view of a first stage of a method of measuring the diameter of a suture, in accordance with one embodiment of the present patent application.
Figure 30B:
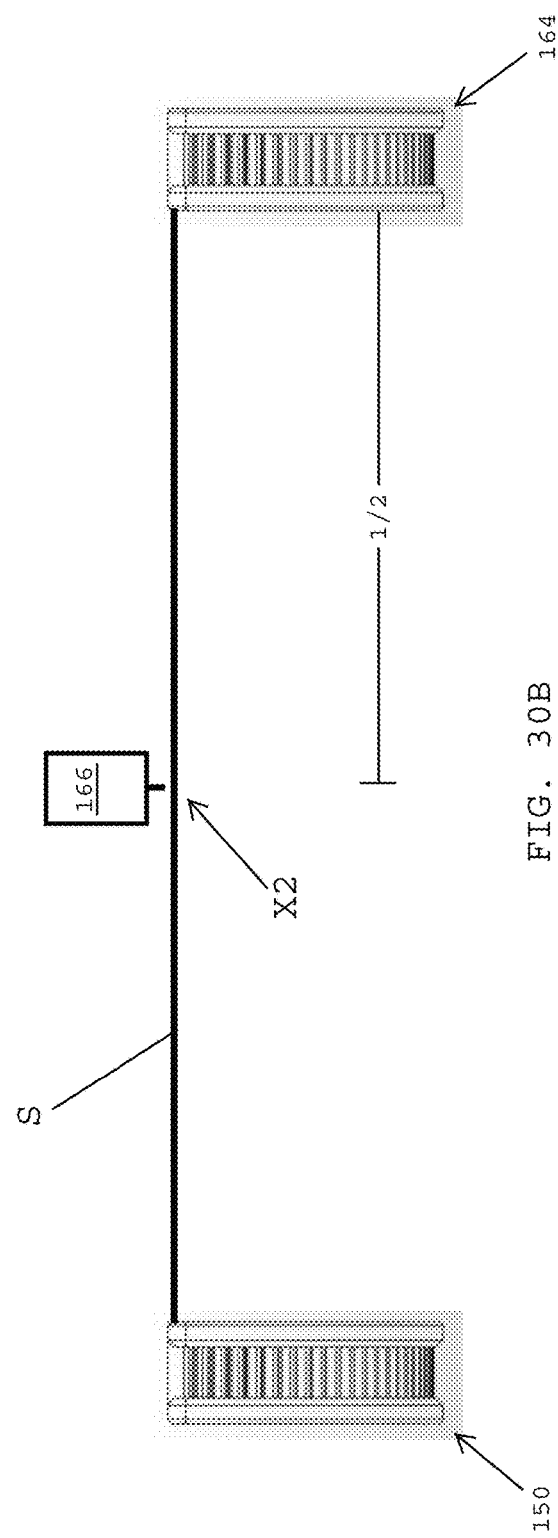
FIG. 30B is a schematic view of a second stage of a method of measuring the diameter of a suture, in accordance with one embodiment of the present patent application.
Figure 30C:
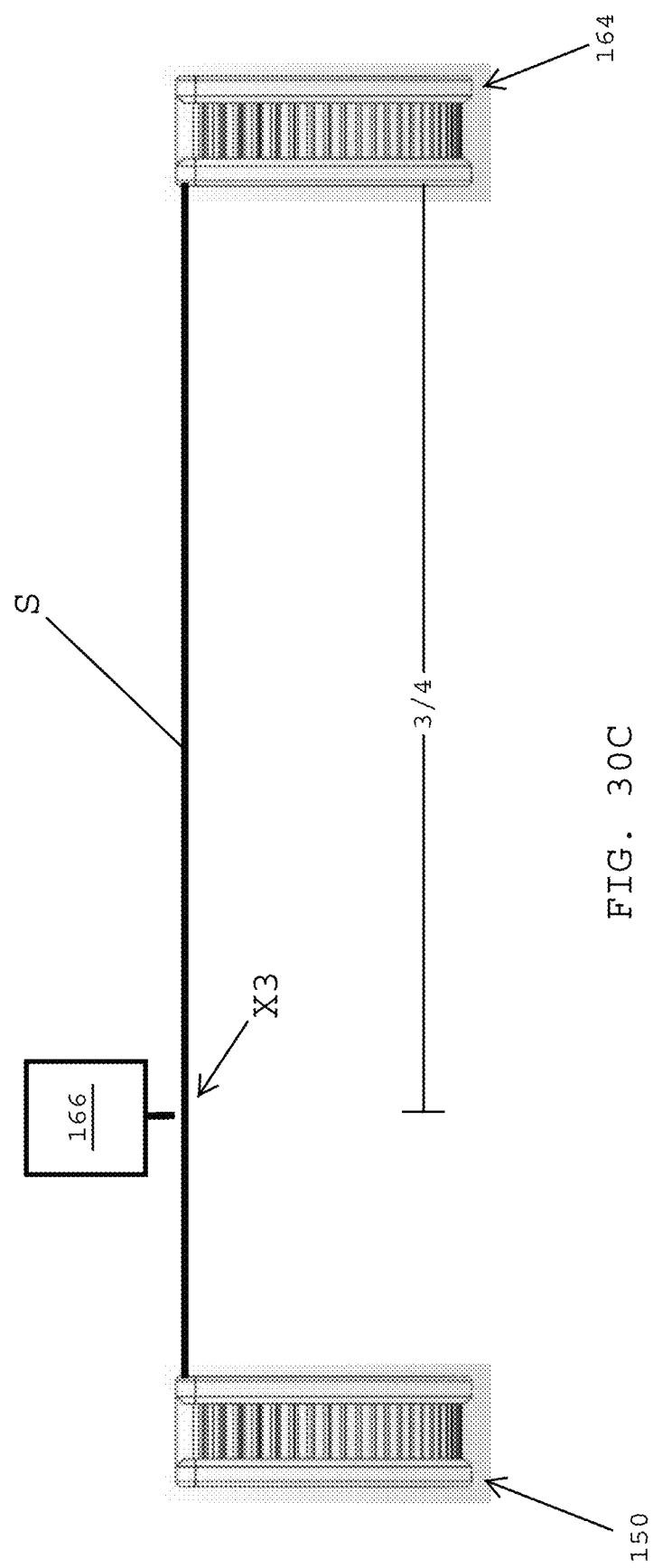
FIG. 30C is a schematic view of a third stage of a method of measuring the diameter of a suture, in accordance with one embodiment of the present patent application.

Referring to FIGS. 30A-30C, in one embodiment, the system 100 preferably includes a suture diameter gauge 166 that may slide between the left and right sides 104, 106 of a test bench 102 (FIG. 23A) for positioning the suture diameter gauge 166 at various selected points along the length of a suture S, which is held taut by first and second suture clamping assemblies 150, 164.

Referring to FIG. 30A, in one embodiment, the system 100 preferably includes the first suture clamping assembly 150 located adjacent a left side 104 of a test bench 102 (FIG. 1) and a second suture clamping assembly 164 located adjacent a right side 106 of the test bench 102 (FIG. 1). The system 100 preferably includes the suture diameter gauge 166 that is slideable between the left and right sides of the test bench for obtaining diameter measurements at different points along the length of the suture S.

Referring to FIG. 30A, in one embodiment, the suture diameter gauge 166 may be moved (e.g., slid along the front and rear guide rails) to a first point designated X1 that is about ¼ of the way along the length of the suture S for obtaining a first set of diameter readings for the suture S at the first point X1. The brake assembly may be deployed for locking the suture diameter gauge in place at the first point X1. In one embodiment, the first set of diameter readings includes obtaining a first diameter reading with the first and second suture clamping assemblies 150, 164 and the suture S in the zero degree position (see FIG. 28B). After the first diameter reading of the suture S has been obtained at the first point X1, the first and second suture clamping assemblies 150, 164 and the suture S may be simultaneously rotated by 90 degrees to the 90 degree position (see FIG. 29). The suture diameter gauge 166 may then be used to obtain a second diameter reading for the suture S at the first point X1, which is 90 degrees away from the first diameter reading. Thus, the first set of suture diameter readings are taken at the first point X1, with a first diameter reading of the first set taken with the suture S in the zero degree position and a second diameter reading of the first set taken with the suture S in the 90 degree position. In one embodiment, the two diameter measurements may be averaged to provide a single diameter measurement that is associated with the point P1 of the suture S.

Referring to FIG. 30B, in one embodiment, the brake assembly may be unlocked and the suture diameter gauge 166 moved (e.g., slid along the front and rear guide rails) to a second point X2 that is about ½ of the way along the length of the suture S for obtaining a second set of diameter readings for the suture S at the second point X2. After being moved to the second point X2, the brake assembly is preferably re-deployed for locking the suture diameter gauge at the second point X2. In one embodiment, the second set of diameter readings includes obtaining a first diameter reading with the first and second suture clamping assemblies 150, 164 and the suture S in the zero degree position (see FIG. 28B). After the first diameter reading of the suture S has been obtained at the second point P2, the first and second suture clamping assemblies 150, 164 and the suture S may be simultaneously rotated on the axis by 90 degrees to the 90 degree position (see FIG. 29). The suture diameter gauge 166 may then be used to obtain a second diameter reading for the suture S at the second point X2, which is 90 degrees away from the first diameter reading for the second set of diameter readings. Thus, the second set of suture diameter readings are taken at the second point X2, with a first diameter reading of the second set taken with the suture S in the zero degree position and a second diameter reading of the second set taken with the suture S in the 90 degree position.

Referring to FIG. 30C, in one embodiment, the brake assembly may be again unlocked so that the suture diameter gauge 166 may be moved (e.g., slid along the front and rear guide rails) to a third point X3 that is about ¾ of the way along the length of the suture S for obtaining a third set of diameter readings for the suture S at the third point X3. After being moved to the third point X3, the brake assembly is preferably re-deployed for locking the suture diameter gauge at the third point X3. In one embodiment, the third set of diameter readings includes obtaining a first diameter reading with the first and second suture clamping assemblies 150, 164 and the suture S in the zero degree position (see FIG. 28B). After the first diameter reading of the suture S has been obtained at the third point X3, the first and second suture clamping assemblies 150, 164 and the suture S may be simultaneously rotated by 90 degrees to the 90 degree position (see FIG. 29). The suture diameter gauge 166 may then be used to obtain a second diameter reading for the suture S at the third point X3, which is 90 degrees away from the first diameter reading for the third set of diameter readings. Thus, the third set of suture diameter readings are desirably taken at the third point X3, with a first diameter reading of the third set taken with the suture S in the zero degree position and a second diameter reading of the third set taken with the suture S in the 90 degree position.

In one embodiment, suture diameter readings may be obtained at more than three different locations along the length of a suture. For example, in one embodiment, first and second suture diameter readings may be obtained every six inches along the length of a 10 foot long suture for a total of 40 readings (i.e., 20 readings with the suture in the first zero degree position and 20 readings with the suture in the second 90 degree position), or every 12 inches along the length of a 10 foot long suture for a total of 20 readings (i.e., 10 readings with the suture in the first zero degree position and 10 readings with the suture in the second 90 degree position).

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A system for measuring the diameter of a suture comprising:
    a test bench;
    a first suture clamping assembly slidably mounted to said test bench;
    a second suture clamping assembly fixed to said test bench;
    a suture diameter gauge slidably mounted to said test bench and located between said first and second suture clamping assemblies;
    a rotation assembly coupled with said first and second suture clamping assemblies for simultaneously rotating said first and second suture clamping assemblies on an axis between a first position and a second position that defines a right angle with the first position; and
    a suture tensioning assembly coupled with one of said first and second suture clamping assemblies.

2. The system as claimed in claim 1, further comprising:
    said first suture clamping assembly including a first suture mounting surface;
    said second suture clamping assembly including a second suture mounting surface, wherein said first and second suture mounting surfaces are configured for simultaneously rotating on the axis when moving between the first position and the second position.

3. The system as claimed in claim 2, wherein said first and second suture mounting surfaces lie in a common horizontal plane when said first and second suture clamping assemblies are in the first position, wherein said first and second suture mounting surfaces lie in a common vertical plane when said first and second suture clamping assemblies are in the second position, and wherein said first and second suture mounting surfaces remain is common planes at all times as they move between the first and second positions.

4. The system as claimed in claim 3, further comprising:
    said first suture clamping assembly including a first suture securing lever having a first cam surface and a first suture backstop that opposes said first cam surface, wherein said first suture securing lever is moveable between an unlocked position and a locked position;
    said second suture clamping assembly including a second suture securing lever having a second cam surface and a second suture backstop that opposes said second cam surface, wherein said second suture securing lever is moveable between an unlocked position and a locked position.

5. The system as claimed in claim 4, further comprising a suture having a first end secured between said first cam surface and said first suture backstop and a second end of said suture secured between said second cam surface and said second suture backstop.

6. The system as claimed in claim 5, wherein said test bench comprises:
    a left end plate that defines a left end of said test bench;
    a right end plate assembly that defines a right end of said test bench;
    a front guide rail interconnecting said left end plate and said right end plate assembly;
    a rear guide rail interconnecting said left end plate and said right end plate assembly, wherein said front and rear guide rails have respective longitudinal axes that are parallel to one another;
    wherein said first suture clamping assembly is slidably mounted on said front and rear guide rails for sliding between said left end plate and said right end plate assembly;
    wherein said suture diameter gauge is slidably mounted on said front and rear guide rails for sliding between said first suture clamping assembly and said right end plate assembly, and wherein said suture diameter gauge comprises a brake assembly for locking said suture diameter gauge at selected locations along the lengths of said respective front and rear guide rails.

7. The system as claimed in claim 6, further comprising:
    said rotation assembly including a rotatable bar having a longitudinal axis;
    said rotatable bar having a first end that is rotatably secured to said left end plate, a second end that is rotatably secured to said right end plate, and said rotatable bar being coupled with said first and second suture clamping assemblies, wherein said rotatable bar is rotatable about the longitudinal axis thereof for moving said first and second suture clamping assemblies between the first position and the second position.

8. The system as claimed in claim 7, further comprising:
    said first suture clamping assembly including a first small gear mounted on said rotatable bar and a first large gear that meshes with said first small gear, wherein said first suture mounting surface is secured to said first large gear;
    said second suture clamping assembly including a second small gear mounted on said rotatable bar and a second large gear that meshes with said second small gear, wherein said second suture mounting surface is secured to said second large gear;

wherein rotating said rotatable bar simultaneously rotates said first and second small gears, which, in turn, simultaneously rotates said respective first and second large gears, which, in turn, simultaneously rotates said respective first and second suture mounting surfaces.

9. The system as claimed in claim 8, further comprising:
a locking handle coupled with said first suture clamping assembly;
said locking handle having an unlocked position in which said first suture clamping assembly is free to slide over said front and rear guide rails and said rotatable bar for adjusting a distance between said first suture clamping assembly and said second suture clamping assembly;
said locking handle having a locked position in which said first suture clamping assembly is locked in place to said front and rear guide rails.

10. The system as claimed in claim 9, further comprising:
said first suture clamping assembly including a first outer gear plate and a first inner gear plate that contain said first small gear and said first large gear, and a first rotatable bar opening passing through said first outer gear plate and said first inner gear plate for receiving said rotatable bar;
said second suture clamping assembly including a second outer gear plate and a second inner gear plate that contain said second small gear and said second large gear, and a second rotatable bar opening passing through said second outer gear plate and said second inner gear plate for receiving said rotatable bar.

11. The system as claimed in claim 10, wherein with said locking handle in the unlocked position, said first suture clamping assembly is free to slide over said front and rear guide rails and said rotatable bar for adjusting the distance between said first suture clamping assembly and said second suture clamping assembly, and wherein said second suture clamping assembly is fixed to an upper end of said right end plate assembly.

12. The system as claimed in claim 6, wherein said test bench comprises:
a left front leg and a left rear leg located at the left side of said test bench;
a left lateral support interconnecting upper ends of said left front leg and said left rear leg;
a right front leg and a right rear leg located at the right side of said test bench;
a right lateral support interconnecting upper ends of said right front leg and said right rear leg;
a longitudinal support extending along a length of said test bench and interconnecting said left and right lateral supports;
a leveling foot mounted at a lower end of each said leg for adjusting respective lengths of said legs and for leveling said test bench.

13. The system as claimed in claim 5, wherein said suture diameter gauge comprises:
a suture testing platform having a top surface adapted to seat a suture;
a test probe having a lower end that is configured to be lowered toward the top surface of said suture testing platform for measuring a diameter of said suture;
a visual display for showing the measured diameter of said suture;
an actuator coupled with said test probe for controlling the movement of the lower end of said test probe toward the top surface of said suture testing platform.

14. A system for measuring the diameter of a suture comprising:
a test bench including a left end plate and a right end plate assembly and front and rear guide rails that extend between said left end plate and said right end plate assembly, wherein said front and rear guide rails have respective longitudinal axes that are parallel to one another;
a first suture clamping assembly slidably mounted to said front and rear guide rails;
a second suture clamping assembly fixed to an upper end of said right end plate assembly;
a suture diameter gauge slidably mounted to said front and rear guide rails;
a rotatable bar coupled with said first and second suture clamping assemblies for simultaneously rotating said first and second suture clamping assemblies on an axis between a first position and a second position that defines a right angle with the first position; and
a suture tensioning assembly coupled with a linear slide and said second suture clamping assembly, wherein said first suture clamping assembly is configured to slide over both said front and rear guide rails and said rotatable bar for adjusting a distance between said first suture clamping assembly and said second suture clamping assembly, and wherein said suture diameter gauge is configured to slide over said front and rear guide rails for obtaining suture diameter measurements at different points between said first and second suture clamping assemblies.

15. The system as claimed in claim 14, wherein said suture diameter gauge comprises a brake assembly for locking said suture diameter gauge at selected locations along the lengths of said respective front and rear guide rails.

16. The system as claimed in claim 14, further comprising:
said rotatable bar having a longitudinal axis that is parallel with the longitudinal axes of said respective front and rear guide rails;
said rotatable bar having a first end that is rotatably coupled with said left end plate, a second end that is rotatably secured to said right end plate assembly, wherein said rotatable bar is rotatable about the longitudinal axis thereof for moving said first and second suture clamping assemblies between the first position and the second position that defines the right angle with the first position.

17. The system as claimed in claim 16, further comprising:
said first suture clamping assembly including a first small gear mounted on said rotatable bar, a first large gear that meshes with said first small gear, and a first suture mounting surface that is secured to said first large gear;
said second suture clamping assembly including a second small gear mounted on said rotatable bar, a second large gear that meshes with said second small gear, and a second suture mounting surface that is secured to said second large gear;
wherein rotating said rotatable bar simultaneously rotates said first and second small gears, which, in turn, simultaneously rotates said respective first and second large gears, which, in turn, simultaneously rotates said respective first and second suture mounting surfaces.

18. The system as claimed in claim 17, further comprising:
said first suture clamping assembly including a first outer gear plate and a first inner gear plate that contain said first small gear and said first large gear, and a first rotatable bar opening passing through said first outer gear plate and said first inner gear plate for receiving said rotatable bar, wherein said first outer gear plate and said first inner gear plate are configured to slide over said rotatable bar;

said second suture clamping assembly including a second outer gear plate and a second inner gear plate that contain said second small gear and said second large gear, and a second rotatable bar opening passing through said second outer gear plate and said second inner gear plate for receiving said rotatable bar.

19. A method of measuring the diameter of a suture comprising:

securing a first end of a suture to a first suture clamping assembly;

securing a second end of said suture to a second suture clamping assembly;

applying tension to said suture through one of said first and second suture clamping assemblies, wherein said suture under tension lies in an axis that extends from said first suture clamping assembly to said second suture clamping assembly;

locating a suture diameter gauge at a first point along a length of said suture;

using said suture diameter gauge to obtain a first diameter measurement for said suture at the first point along the length of said suture;

while continuing to apply the tension to said suture, simultaneously rotating said first and second suture clamping assemblies on the axis by 90 degrees between a first position and a second position, which, in turn, rotates said suture on the axis by 90 degrees between the first and second positions;

using said suture diameter gauge to obtain a second diameter measurement for said suture at the first point along the length of said suture, wherein the first and second diameter measurements at the first point along the length of said suture are at a right angle relative to one another.

20. The method as claimed in claim 19, further comprising:

simultaneously rotating said first and second suture clamping assemblies back to the first position, which, in turn, rotates said suture on the axis by 90 degrees back to the first position;

moving said suture diameter gauge to a second point along the length of said suture that is spaced from the first point;

while continuing to apply the tension to said suture, using said suture diameter gauge to obtain a first diameter measurement for said suture at the second point along the length of said suture;

while continuing to apply the tension to said suture, simultaneously rotating said first and second suture clamping assemblies on the axis by 90 degrees, which, in turn, rotates said suture on the axis by 90 degrees;

using said suture diameter gauge to obtain a second diameter measurement for said suture at the second point along the length of said suture, wherein the first and second diameter measurements at the second point along the length of said suture are at a right angle relative to one another.

21. The method as claimed in claim 20, further comprising:

simultaneously rotating said first and second suture clamping assemblies back to the first position;

moving said suture diameter gauge to a third point along the length of said suture that is spaced from the second point;

while continuing to apply the tension to said suture, using said suture diameter gauge to obtain a first diameter measurement for said suture at the third point along the length of said suture;

while continuing to apply the tension to said suture, simultaneously rotating said first and second suture clamping assemblies on the axis by 90 degrees, which, in turn, rotates said suture on the axis by 90 degrees;

using said suture diameter gauge to obtain a second diameter measurement for said suture at the third point along the length of said suture, wherein the first and second diameter measurements at the third point along the length of said suture are at a right angle relative to one another.

* * * * *